United States Patent
Wendeborn et al.

(10) Patent No.: US 10,934,262 B2
(45) Date of Patent: Mar. 2, 2021

(54) HETEROCYCLIC BRIDGED BIPHENYLS

(71) Applicant: UDC IRELAND LIMITED, Dublin (IE)

(72) Inventors: Frederique Wendeborn, Dublin (IE); Beat Schmidhalter, Dublin (IE); Thomas Schäfer, Dublin (IE); Peter Murer, Dublin (IE); Kristina Bardon, Dublin (IE)

(73) Assignee: UDC IRELAND LIMITED, Dublin (IE)

(*) Notice: Subject to any disclaimer, the term of this patent is extended or adjusted under 35 U.S.C. 154(b) by 378 days.

(21) Appl. No.: 15/910,568

(22) Filed: Mar. 2, 2018

(65) Prior Publication Data

US 2018/0258053 A1    Sep. 13, 2018

Related U.S. Application Data

(63) Continuation of application No. 12/310,737, filed as application No. PCT/EP2007/059218 on Sep. 4, 2007, now abandoned.

(30) Foreign Application Priority Data

Sep. 24, 2006    (EP) ..................... 06120674

(51) Int. Cl.
*H01L 51/50* (2006.01)
*C07D 235/18* (2006.01)
(Continued)

(52) U.S. Cl.
CPC ......... *C07D 235/18* (2013.01); *C07D 209/58* (2013.01); *C07D 241/42* (2013.01);
(Continued)

(58) Field of Classification Search
None
See application file for complete search history.

(56) References Cited

U.S. PATENT DOCUMENTS 8,138,303 B2   3/2012   Chebotareva
9,028,979 B2   5/2015   Schildknecht
(Continued)

FOREIGN PATENT DOCUMENTS

JP   02134644   * 5/1990 ............. G03G 5/147
JP   H02134644 A    5/1990
(Continued)

OTHER PUBLICATIONS

English language machine-generated translation of JP2000-323278 (14 Pages); 2000.
(Continued)

*Primary Examiner* — Gregory D Clark
(74) *Attorney, Agent, or Firm* — Riverside Law LLP

(57) ABSTRACT

The present invention relates electroluminescent devices, comprising a compound of the formula

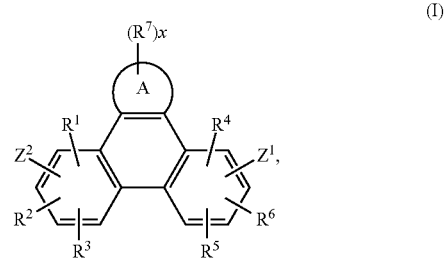

especially as host for phosphorescent compounds. The hosts may function with phosphorescent materials to provide improved efficiency, stability, manufacturability, or spectral characteristics of electroluminescent devices.

11 Claims, 1 Drawing Sheet

(51) Int. Cl.
  *C07D 209/58* (2006.01)
  *C07D 241/42* (2006.01)
  *C07D 263/57* (2006.01)
  *C07D 403/14* (2006.01)
  *C07D 413/14* (2006.01)
  *C07F 9/6506* (2006.01)
  *C07F 9/653* (2006.01)

(52) U.S. Cl.
  CPC ......... *C07D 263/57* (2013.01); *C07D 403/14* (2013.01); *C07D 413/14* (2013.01); *C07F 9/65068* (2013.01); *C07F 9/65324* (2013.01)

(56) References Cited

U.S. PATENT DOCUMENTS

| | | |
|---|---|---|
| 2006/0163562 A1 | 7/2006 | Boerner |
| 2006/0289882 A1 | 12/2006 | Nishimura |
| 2007/0029927 A1 | 2/2007 | Kawamura |
| 2009/0026919 A1 | 1/2009 | Stossel |
| 2009/0105447 A1 | 4/2009 | Schafer |
| 2010/0249349 A1 | 9/2010 | Chebotareva |

FOREIGN PATENT DOCUMENTS

| | | |
|---|---|---|
| JP | 09013025 | 1/1997 |
| JP | H11251063 A | 9/1999 |
| JP | 2000323278 | 11/2000 |
| JP | 2001023777 A | 1/2001 |
| JP | 2001118683 | 4/2001 |
| JP | 2002050473 | 2/2002 |
| JP | 2002367786 | 12/2002 |
| JP | 2003059670 | 2/2003 |
| JP | 2007189001 | 7/2007 |
| WO | 02060910 A1 | 8/2002 |
| WO | 2005004251 A1 | 1/2005 |
| WO | 2005019373 A2 | 3/2005 |
| WO | 2005123737 | 12/2005 |

OTHER PUBLICATIONS

English language machine-generated translation of JP2001-118683 (9 Pages); 2001.
English language machine-generated translation of JP2002-050473 (8 Pages); 2002.
English language machine-generated translation of JP2002-367786 (11 Pages); 2002.
English language machine-generated translation of JP2003-059670 (14 Pages); 2003.
English language machine-generated translation of JP2006-143845 (34 Pages); 2006.
English language machine-generated translation of JP2007-189001 (34 Pages); 2007.
Full translation of JP 2001-023777 (publication date Jan. 2001) by Schreiber Translations, Inc.
Machine-generated translation for JP 09-013025 A, which was published Jan. 1997.
Machine-generated translation for JP 11-251063 A, which was published Sep. 1999.
Machine-generated translation for JP 2001-023777 A, which was published Jan. 2001.
Partial translation by USPTO translator of JP 2001-023777 (which was published on Jan. 2001).
Patent Abstracts of Japan Pub. No. 02134644, May 23, 1990.
Patent Abstracts of Japan Pub. No. 09013025, Jan. 14, 1997.
Patent Abstracts of Japan Pub. No. 11251063, Sep. 17, 1999.
Patent Abstracts of Japan Pub. No. 2001023777, Jan. 26, 2001.
Translator-generated English translation for JP 2001-023777 A (publication date Jan. 2001).
Twieg et al., SPIE vol. 2025, (1993), pp. 94-105.
Vol. 1990, No. 27, Database accession No. 1990-204552, XP002419353.
Yershi, Hartmut, ed., Highly Efficient OLEDs with Phosphorescent Materials, Weinham, Germany: Wiley-VCH, 2008, pp. 385-386. Print.

\* cited by examiner

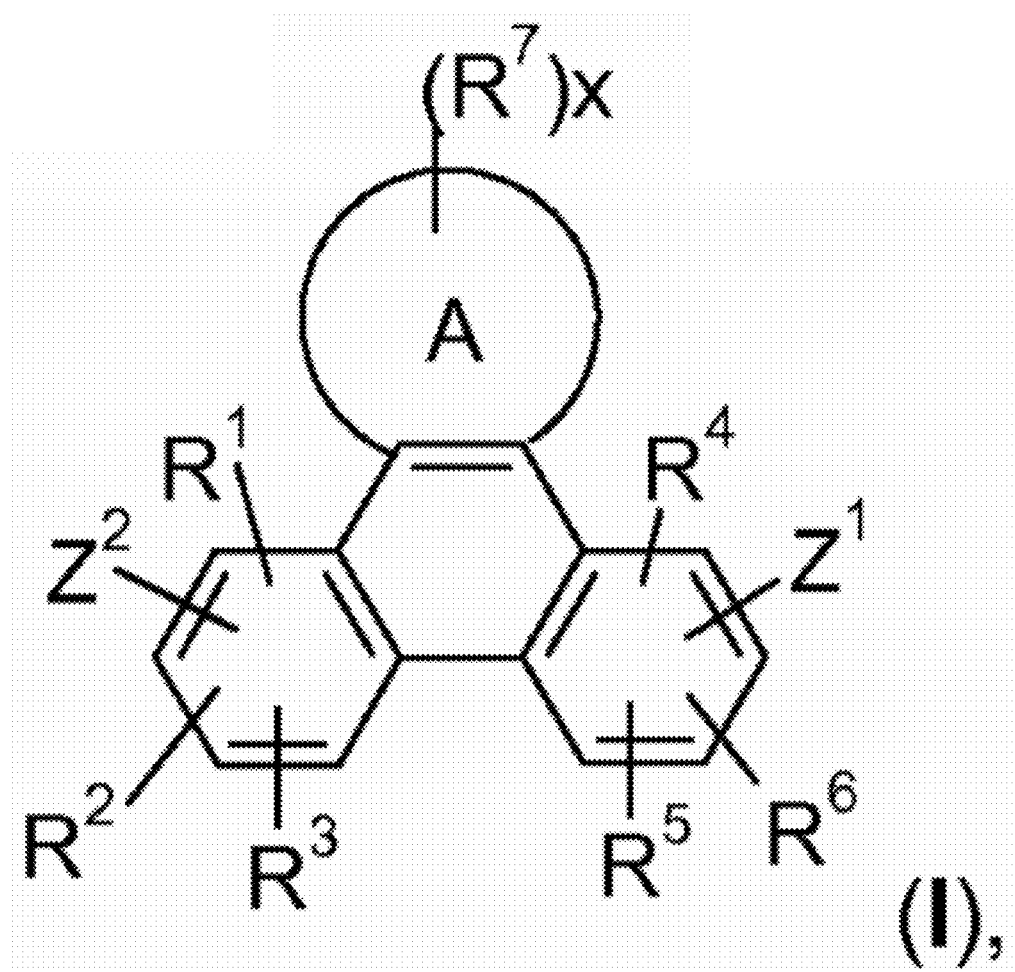

HETEROCYCLIC BRIDGED BIPHENYLS

CROSS-REFERENCE TO RELATED APPLICATIONS

The present application is a continuation of U.S. patent application Ser. No. 12/310,737, filed Mar. 5, 2009, which is the U.S. National Stage Application filed under 35 U.S.C. § 371 of International Patent Application No. PCT/EP2007/059218, filed Sep. 4, 2007, which claims priority to European Patent Application No. 06120674.7, filed Sep. 14, 2006, all of which applications are hereby incorporated by reference in their entireties.

The present invention relates electroluminescent devices, comprising a compound of the formula

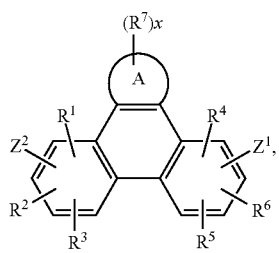

(I)

especially as host for phosphorescent compounds. The hosts may function with phosphorescent materials to provide improved efficiency, stability, manufacturability, or spectral characteristics of electroluminescent devices.

JP9013025 relates to an electroluminescent element a quinoxaline derivative represented by the formula

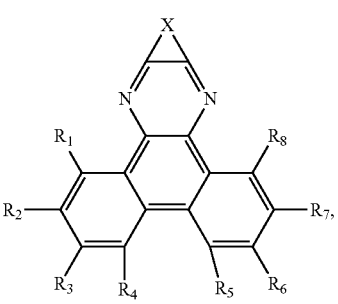

wherein X is a $C_2$-$C_5$alkyl or the like; and $R_1$ to $R_8$, which are independent of each other, are each H, a halogen, a $C_1$-$C_6$alkyl or the like.

JP11251063 discloses triphenylene compounds expressed by the formula

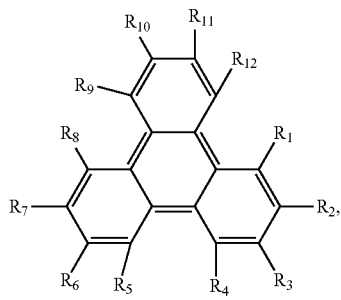

which are used as a component material of an organic EL element.

In the formula, $R_1$ to $R_{12}$ each independently represent an hydrogen atom, a halogen atom, a hydroxyl group, a substituted or unsubstituted amino group, a nitro group, a cyano group, a substituted or unsubstituted alkyl group, a substituted or unsubstituted alkenyl group, a substituted or unsubstituted cycloalkyl group, a substituted or unsubstituted alkoxy group, a substituted or unsubstituted aromatic hydrocarbon group, a substituted or unsubstituted aromatic heterocycle group, a substituted or unsubstituted aralkyl group, a substituted or unsubstituted aryloxy group, a substituted or unsubstituted alkoxycarbonyl group, or a carboxyl group. $R_1$ to $R_{12}$ may form two rings out of them.

JP2006143845 relates to compounds of formula

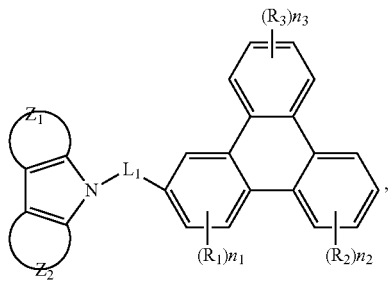

wherein $Z_1$, $Z_2$ are an aromatic hydrocarbon ring, aromatic heterocyclic ring; $R_1$ to $R_3$ are H, substituent; n1=0 to 3; n2, n3=0 to 4; L1=linkage group, single bond).

JP2134644 relates to an electrophotographic sensitive body having a phenazine compound in a photosensitive layer. The phenazine compound is expressed by formula

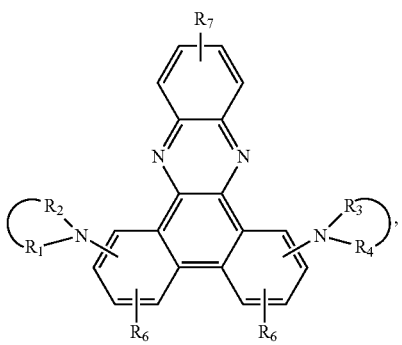

wherein each $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each $R_5$-$R_7$ is an H atom, (substituted)alkyl group, alkoxy group, halogen atom or nitro group.

US20060289882 relates to an organic electroluminescent device, wherein the electron extracting layer may be formed of a hexaazatriphenylene derivative represented by the following structural formula

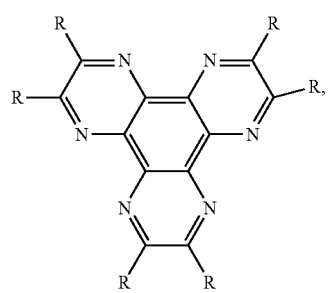

wherein R represents hydrogen, an alkyl group having a carbon number of 1 to 10, an alkyloxy group having a carbon number of 1 to 10, a dialkylamine group having a carbon number of 1 to 10, F, Cl, Br, I or CN.

US20070029927 discloses aromatic amine derivative represented by the following general formula (1):

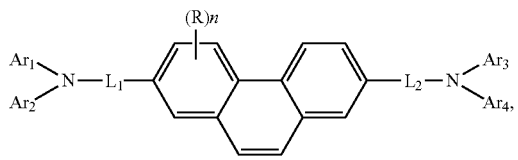

wherein $Ar_1$ to $Ar_4$ each independently represents a substituted or unsubstituted aryl group having 6 to 30 ring carbon atoms or a substituted or unsubstituted heteroaryl group having 5 to 30 ring carbon atoms;

$L_1$ and $L_2$ each independently represents a single bond, a substituted or unsubstituted arylene group having 6 to 30 ring carbon atoms or a substituted or unsubstituted heteroarylene group having 5 to 30 ring carbon atoms;

when both $L_1$ and $L_2$ are single bonds, however, a case where both $Ar_1$ and $Ar_3$ each represents a substituted or unsubstituted phenyl group and further, where both $Ar_2$ and $Ar_4$ each represents a substituted or unsubstituted biphenylyl group or a substituted or unsubstituted phenyl group is excluded; R represents a substituent and when R exists two or more, they may bond each other to form a ring; and n represents an integer of 0 to 8 and their use in organic electroluminescence devices.

JP2134644 relates to phenazine compounds of formula

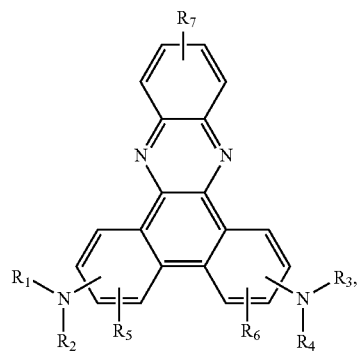

wherein each of $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each of $R_5$-$R_7$ is an H atom, (substituted)alkyl group, alkoxy group, halogen atom or nitro group. When the phenazine compounds are incorporated into a photosensitive layer of an electrophotographic sensitive body.

JP2000323278 relates to an emitter including an organic phosphor having an imidazole structure of the formula

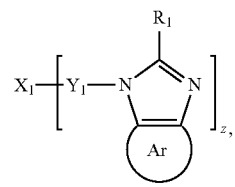

wherein $R_1$ may be either same or different respectively and selected from hydrogen, an alkyl group, a cycloalkyl group, an aralkyl group, an alkenyl group, a cycloalkenyl group, etc., $X_1$ is a bonding unit and selected from a substituted or non-substituted aromatic ring, heterocycle, a saturated fat chain, etc., $Y_1$ is selected from a single bond or a combination of either of single bond, an alkyl chain, an alkylene chain, an ether chain, etc., and Ar is selected from a substituted or non-substituted aromatic ring, heterocycle, etc. and z expresses a natural number. The organic phosphor is preferably a light emitting material having a guest material doped in a host material.

JP 2001023777 describes compounds of the formula

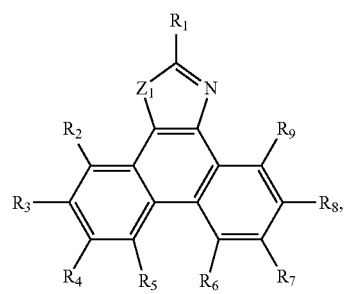

wherein $R_1$ to $R_9$ represent bonding, hydrogen, an alkyl group, a cycloalkyl group, an aralkyl group, an alkenyl group, a cycloalkenyl group, an alkoxy group, an alkylthio group, an arylether group, an aryl thioether group, an aryl group, a heterocyclic group, halogen, a cyano group, an aldehyde group, a carbonyl group, an ester group, a carbamoyl group, an amino group, a nitro group, a silyl group, a siloxyanyl group, and ring structure formed between adjacent substituting groups, and $Z_1$ represents oxygen, sulfur, nitrogen, or saturated hydrocarbon. The compounds having a phenanthroazole skeleton are suitable as a host material or a dopant material in a material of a hole transport layer, an electron transport layer, and a luminescent layer. No compounds, wherein any of $R_1$ to $R_9$ is an aryl substituted amino group are disclosed.

JP2001118683 relates to a luminescent element, wherein the luminescent material is at least composed of a guest material and a host material and the peak of the emission spectrum of the host material is more than 300 nm and less than 460 nm. The following phenanthroazole compound is explicitly disclosed:

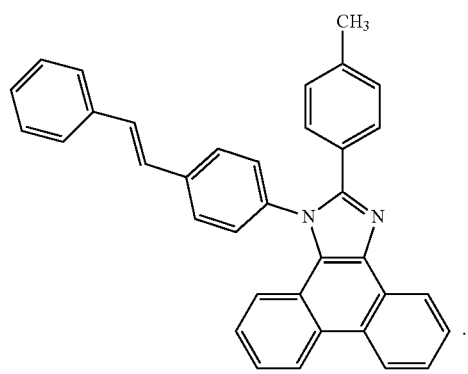 [SMILES: Cc1ccc(-c2nc3c4ccccc4c4ccccc4c3n2-c2ccc(/C=C/c3ccccc3)cc2)cc1]

JP2002050473 describes an element, in which a light emitting substance exists between a positive electrode and a negative electrode and which emits light by electric energy, and the element contains at least one kind of product formed by a photoreaction. The following phenanthroazole compound is explicitly disclosed:

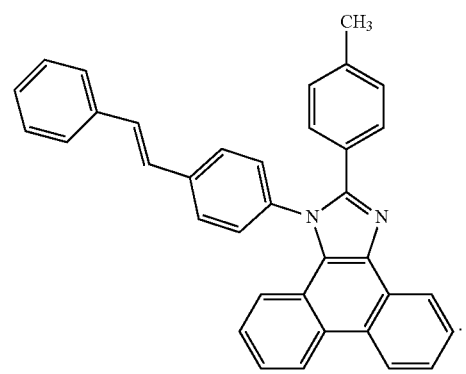 [SMILES: Cc1ccc(-c2nc3c4ccccc4c4ccccc4c3n2-c2ccc(/C=C/c3ccccc3)cc2)cc1]

JP2003059670 describes a light-emitting element having a structure in which at least a positive electrode, a luminous layer, an electron carrier layer, and a negative electrode are laminated in order, the electron carrier layer has an ionization potential 0.1 eV or more larger than the ionization potential of the luminous layer, and the material that mainly constitutes the luminous layer and the electron carrier layer is made of an organic compound having sublimation performance, and further, the organic compound that mainly constitutes the electron carrier layer has a molecular weight of 400 or more and a glass transition temperature of 90° C. or more. The following phenanthroazole compound is explicitly disclosed:

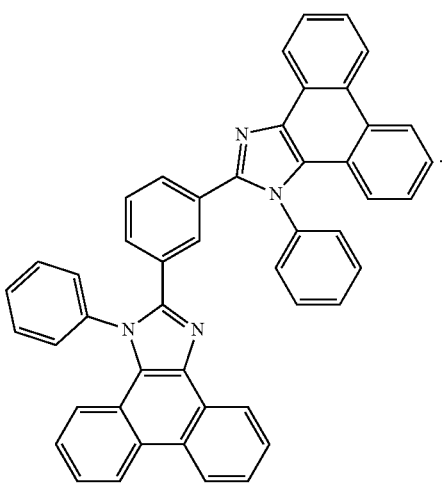 [SMILES: c1ccc(-n2c(-c3cccc(-c4nc5c6ccccc6c6ccccc6c5n4-c4ccccc4)c3)nc3c4ccccc4c4ccccc4c32)cc1]

JP2002367786 describes a luminous element having a sequentially laminated structure of at least a positive electrode, a luminous layer, a hole transport layer, an electron transport layer and a negative electrode, the relation between the luminous layer and the electron transport layer is (Ip(ETL)-Ip(EML))>(Ea(ETL)-Ea(EML)). The main material composing the luminous layer and the electron transport layer is made of an organic compound with sublimatic nature, and the main material composing the electron transport layer is an organic compound with molecular mass of not less than 400. [Ea: electron affinity (eV), Ip: ionization potential (eV), EML: luminous layer, and ETL: electron transport layer]. The following phenanthroazole compound is explicitly disclosed:

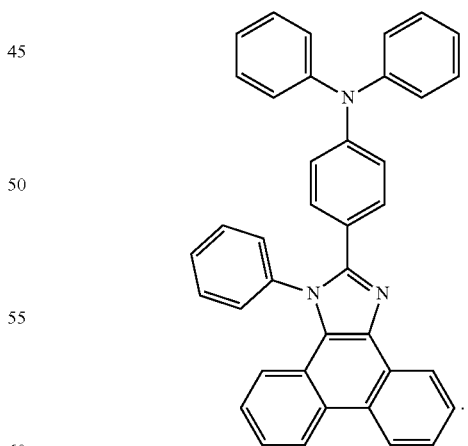

Notwithstanding these developments, there remains a need for EL devices comprising new host materials, and especially hosts that will function with phosphorescent materials to provide improved efficiency, stability, manufacturability, or spectral characteristics of electroluminescent devices.

BRIEF DESCRIPTION OF THE DRAWINGS

FIG. 1 shows Formula (I).

Accordingly, the present invention provides an EL device, comprising a compound of the formula

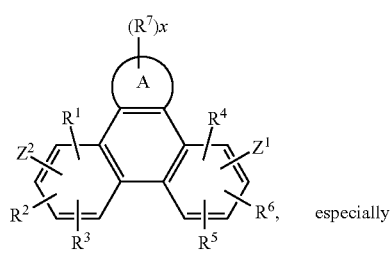

(I)

especially

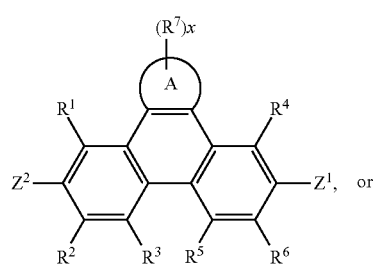

(Ia)

or

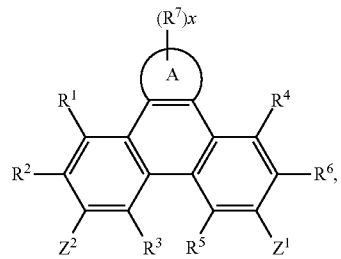

(Ib)

wherein A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur, $Z^1$ is

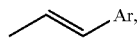

$-NA^1A^{1'}$, $-P(=O)A^4A^{4'}$, or $-SiA^6A^7A^8$, $Z^2$ is

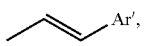

$-NA^2A^{2'}$, $-P(=O)A^5A^{5'}$, or $-SiA^{6'}A^{7'}A^{8'}$,

Ar and Ar' are independently of each other $C_6$-$C_{14}$aryl, such as phenyl, or naphthyl, which may optionally be substituted by one or more groups selected from $C_1$-$C_{25}$alkyl, which may optionally be interrupted by —O—, or $C_1$-$C_{25}$alkoxy, $R^1$, $R^2$, $R^3$, $R^4$, $R^5$ and $R^6$ are independently of each other hydrogen, halogen, or an organic substituent, or $R^1$ and $R^2$, $R^4$ and $R^6$, $R^2$ and $R^3$, $R^5$ and $R^3$ and/or $R^5$ and $R^6$, which are adjacent to each other, together form an aromatic, or heteroaromatic ring, or ring system, which can optionally be substituted, $R^7$ is an organic substituent, wherein two or more substituents $R^7$ in the same molecule may have different meanings, or can form together an aromatic, or heteroaromatic ring, or ring system, and x is 0, or an integer of 1 to 5;

$A^1$, $A^2$, $A^{1'}$ and $A^{2'}$ are independently of each other a $C_6$-$C_{24}$aryl group, a $C_2$-$C_{30}$heteroaryl group, which can optionally be substituted, or a group

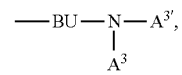

wherein BU is a bridging unit, such as

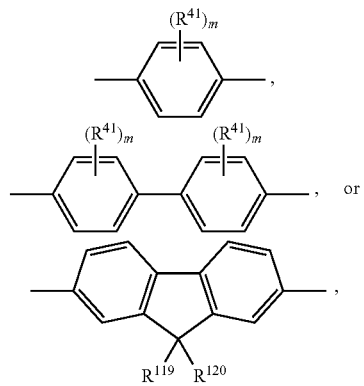

$A^3$ and $A^{3'}$ are independently of each other a $C_6$-$C_{24}$aryl group, or a $C_2$-$C_{30}$heteroaryl group, which can optionally be substituted, or $A^1$ and $A^{1'}$ or $A^2$ and $A^{2'}$ or $A^3$ and $A^{3'}$ together with the nitrogen atom to which they are bonded form a heteroaromatic ring, or ring system, such as

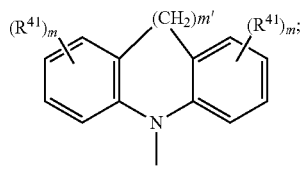

m' is 0, 1, or 2;

$A^4$, $A^{4'}$, $A^6$, $A^7$, $A^8$, $A^2$, $A^{2'}$, $A^5$, $A^{5'}$, $A^{6'}$, $A^{7'}$, and $A^{8'}$ are independently of each other a $C_6$-$C_{24}$aryl group, or a $C_2$-$C_{30}$heteroaryl group, which can optionally be substituted, $R^{41}$ can be the same or different at each occurrence and is Cl, F, CN, $NR^{45}R^{45'}$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by $-NR^{45}-$, $-O-$, $-S-$, $-C(=O)-O-$, or $-O-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ and $R^{45'}$ are independently of each other H, a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is H, a $C_1$-$C_{25}$alkyl group, or a $C_4$-$C_{18}$cycloalkyl group, m can be the same or different at each occurrence and is 0, 1, 2, or 3, especially 0, 1, or 2, very especially 0 or 1.

In addition, the present invention relates to compounds of the formula

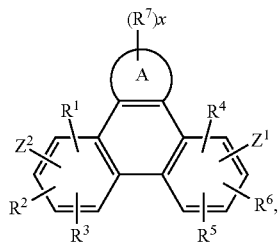
(I)

especially

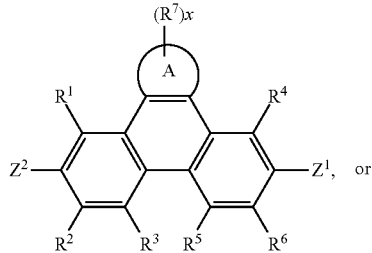
(Ia)

or

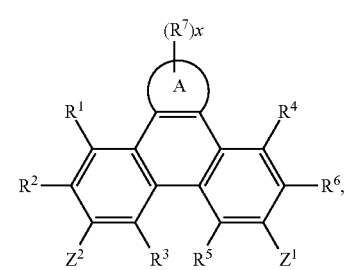
(Ib)

wherein

A, $Z^1$, $Z^2$, $R^1$, $R^2$, $R^3$, $R^4$, $R^5$, $R^6$, $R^7$ and x are as defined in claim 1, with the proviso that phenazine compounds expressed by formula

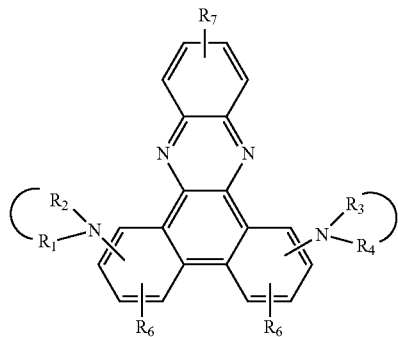

are excluded, wherein each $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each $R_5$-$R_7$ is an H atom, (substituted)alkyl group, alkoxy group, halogen atom or nitro group.

The compounds of formula I can be used in organic light emitting diodes (OLEDs), especially as hosts for phosphorescent compounds. Accordingly, the present invention also provides an electroluminescent device comprising a cathode, an anode, and therebetween a light emitting layer containing a host material and a phosphorescent light-emitting material wherein the host material is a compound of formula I.

Examples of $Z^1$ and $Z^2$ are

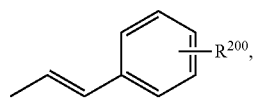

wherein $R^{200}$ is $C_1$-$C_{25}$alkyl, which may optionally be interrupted by —O—, or $C_1$-$C_{25}$alkoxy;

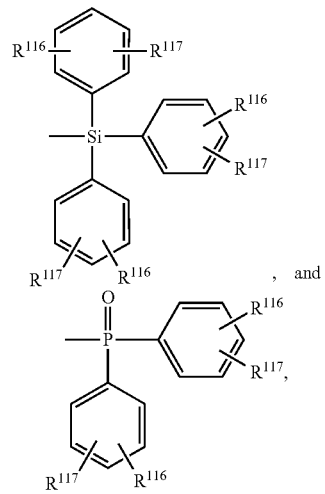
, and wherein $R^{116}$ and $R^{117}$ are as defined below. $Z^1$ is preferably a group

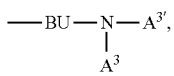

or —$NA^1A^{1'}$. $Z^2$ is preferably a group

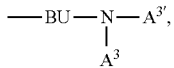

or —$NA^2A^{2'}$. $Z^1$ and $Z^2$ may be different, but are preferably the same.

A is a 5-, 6-, or 7-membered heteroaromatic ring, containing one heteroatom selected from nitrogen, oxygen and sulphur, which can be substituted and/or can be part of a fused aromatic or heteroaromatic ring system. Non-limiting examples of A are:

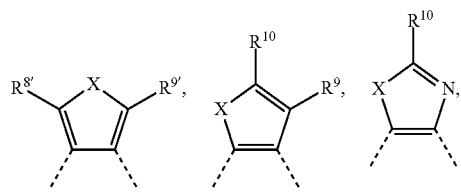

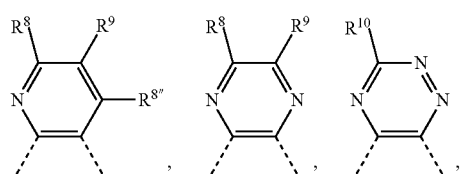

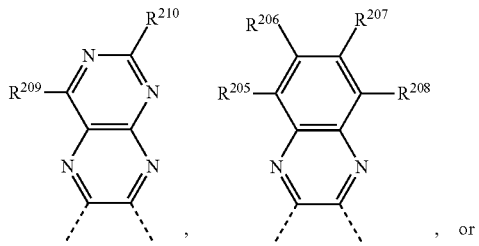

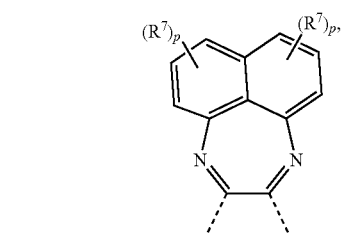

wherein $R^7$ has the meaning of $R^8$, $R^{8'''}$ has the meaning of $R^8$, X is O, S, N—$R^{17}$, wherein $R^{205}$, $R^{206}$, $R^{207}$, $R^{208}$, $R^{209}$, $R^{210}$, $R^8$, $R^9$, $R^{8'}$, $R^{9'}$, $R^{10}$ and $R^{17}$ are as defined below, p is 0, 1, 2, or 3 and the dotted line --- indicates the bonding to the benzene ring.

Preferably, the compound of formula I is a compound according of formula:

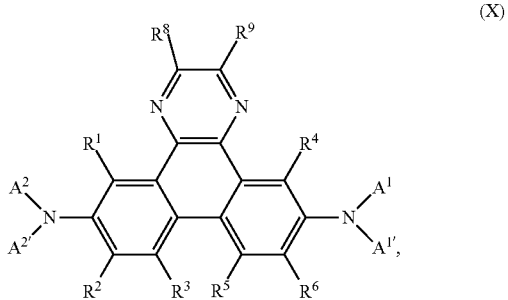

(X)

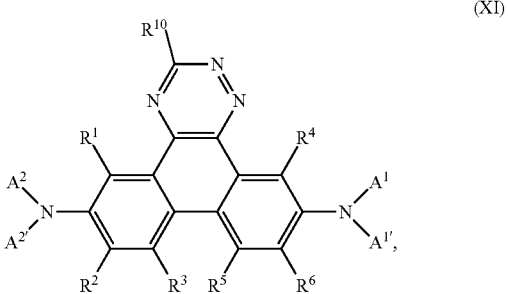

(XI)

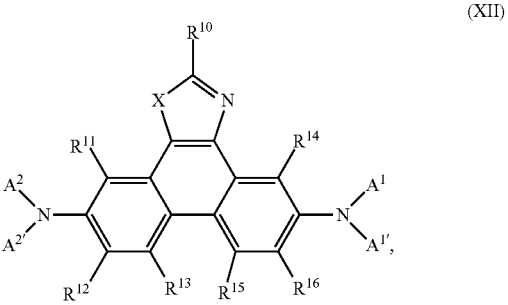

(XII)

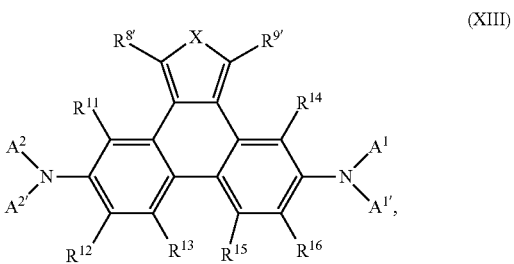

(XIII)

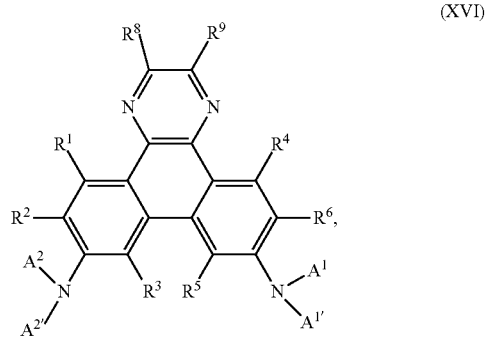

(XVI)

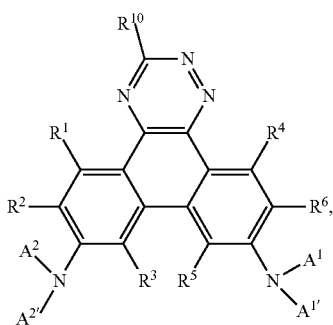

(XVII)

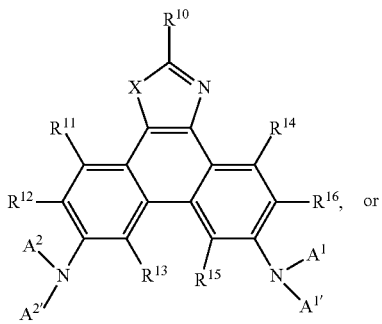

(XVIII)

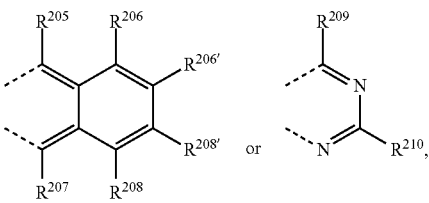

(XIX)

R¹ and R⁴ are independently of each other hydrogen, halogen, C₁-C₁₈alkyl, C₁-C₁₈alkyl which is substituted by E and/or interrupted by D, C₁-C₁₈perfluoroalkyl, C₂-C₁₈alkenyl, C₂-C₁₈alkynyl, C₁-C₁₈alkoxy, C₁-C₁₈alkoxy which is substituted by E and/or interrupted by D, CN, or —CO—R²⁸, R², R³, R⁵ and R⁶ are independently of each other H, halogen, C₁-C₁₈alkyl, C₁-C₁₈alkyl which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₁-C₁₈alkoxy, C₁-C₁₈alkoxy which is substituted by E and/or interrupted by D, C₇-C₂₅aralkyl, CN, or —CO—R²⁸, R⁸ and R⁹ are independently of each other H, C₁-C₁₈alkyl, C₁-C₁₈alkyl which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₁-C₁₈alkoxy, C₁-C₁₈alkoxy which is substituted by E and/or interrupted by D, C₇-C₂₅aralkyl, CN, or —CO—R²⁸, or R⁸ and R⁹ together form a group

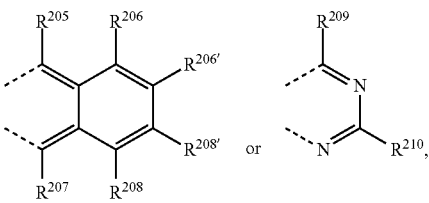

wherein R²⁰⁶', R²⁰⁸', R²⁰⁵, R²⁰⁶, R²⁰⁷, R²⁰⁸, R²⁰⁹ and R²¹⁰ are independently of each other H, C₁-C₁₈alkyl, C₁-C₁₈alkyl which is substituted by E and/or interrupted by D, C₁-C₁₈alkoxy, or C₁-C₁₈alkoxy which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₇-C₂₅aralkyl, CN, or —CO—R²⁸, R¹⁰ is H, C₁-C₁₈alkyl, C₁-C₁₈alkyl which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₁-C₁₈alkoxy, C₁-C₁₈alkoxy which is substituted by E and/or interrupted by D, C₇-C₂₅aralkyl, or —CO—R²⁸, R⁸' and R⁹' are independently of each other H, CN, —COOR²⁷; —CONR²⁵R²⁶, C₁-C₁₈alkyl, C₁-C₁₈alkyl which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₁-C₁₈alkoxy, C₁-C₁₈alkoxy which is substituted by E and/or interrupted by D, C₇-C₂₅aralkyl, CN, or —CO—R²⁸;

R¹¹ and R¹⁴ are independently of each other hydrogen, halogen, C₁-C₁₈alkyl, C₁-C₁₈alkyl which is substituted by E and/or interrupted by D, C₁-C₁₈perfluoroalkyl, C₂-C₁₈alkenyl, C₂-C₁₈alkynyl, C₁-C₁₈alkoxy, C₁-C₁₈alkoxy which is substituted by E and/or interrupted by D, CN, or —CO—R²⁸, R¹², R¹³, R¹⁵ and R¹⁶ are independently of each other H, halogen, C₁-C₁₈alkyl, C₁-C₁₈alkyl which is substituted by E and/or interrupted by D, C₁-C₁₈perfluoroalkyl, C₆-C₂₄aryl, C₆-C₂₄aryl which is substituted by G, C₂-C₂₀heteroaryl, C₂-C₂₀heteroaryl which is substituted by G, C₂-C₁₈alkenyl, C₂-C₁₈alkynyl, C₁-C₁₈alkoxy, C₁-C₁₈alkoxy which is substituted by E and/or interrupted by D, C₇-C₂₅aralkyl, CN or —CO—R²⁸, X is O, S, or NR¹⁷, wherein R¹⁷ is H; C₆-C₁₈aryl; C₂-C₂₀heteroaryl; C₆-C₁₈aryl, or C₂-C₂₀heteroaryl, which are substituted by C₁-C₁₈alkyl, C₁-C₁₈perfluoroalkyl, or C₁-C₁₈alkoxy; C₁-C₁₈alkyl; or C₁-C₁₈alkyl which is interrupted by —O—;

or two substituents $R^1$ and $R^2$, $R^4$ and $R^6$, $R^{11}$ and $R^{12}$, and/or $R^{14}$ and $R^{16}$, $R^2$ and $R^3$, $R^5$ and $R^6$, $R^{12}$ and $R^{13}$, and/or $R^{15}$ and $R^{16}$, which are adjacent to each other, together form a group

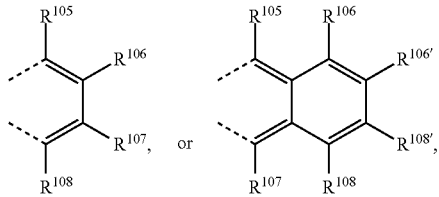

or two substituents $R^{15}$ and $R^{13}$, and/or $R^5$ and $R^3$, which are adjacent to each other, together form a group

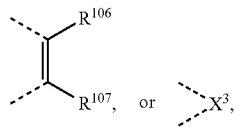

wherein $X^3$ is O, S, $C(R^{119})(R^{120})$, or $NR^{17}$, wherein $R^{17}$ is as defined above, $R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula $=CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{127}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—; —COO—; —S—; —SO—; —$SO_2$—; —O—; —$NR^{25}$—; —$SiR^{30}R^{31}$—; —$POR^{32}$—; —$CR^{23}=CR^{24}$—; or —C≡C—; and E is —$OR^{29}$; —$SR^{29}$; —$NR^{25}R^{26}$; —$COR^{28}$; —$COOR^{27}$; —$CONR^{25}R^{26}$; —CN; or halogen; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, $R^{27}$ and $R^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, and $A^1$, $A^2$, $A^{1'}$ and $A^{2'}$ are as defined above.

Preferably, $R^{116}$ and $R^{117}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is substituted by E and/or interrupted by D, such as —$CH_2OCH_3$, —$CH_2OCH_2CH_3$, —$CH_2OCH_2CH_2OCH_3$, or —$CH_2OCH_2CH_2OCH_2CH_3$, $C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as —$C_6H_4OCH_3$, —$C_6H_4OCH_2CH_3$, —$C_6H_3(OCH_3)_2$, or —$C_6H_3(OCH_2CH_3)_2$, —$C_6H_4CH_3$, —$C_6H_3(CH_3)_2$, —$C_6H_2(CH_3)_3$, or —$C_6H_4tBu$.

X is O, S, or $NR^{17}$. In case of compounds of formula XII and XVIII X is preferably O, or $NR^{17}$. In case of compounds of formula XIII and XIX X is preferably S, or $NR^{17}$.

$R^{17}$ is preferably H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, n-heptyl, or $C_6$-$C_{14}$aryl, such as phenyl, naphthyl, or biphenylyl.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —$CH_2(OCH_2CH_2)_wOCH_3$, w=1, 2, 3, or 4, $C_6$-$C_{14}$aryl, such as phenyl, naphthyl, or biphenylyl, $C_6$-$C_{14}$aryl which is substituted by G, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

D is preferably —CO—, —COO—, —S—, —SO—, —$SO_2$—, —O—, —$NR^{25}$—, wherein $R^{25}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, naphthyl, or biphenylyl.

E is preferably —$OR^{29}$; —$SR^{29}$; —$NR^{25}R^{25}$; —$COR^{28}$; —$COOR^{27}$; —$CONR^{25}R^{25}$; or —CN; wherein $R^{25}$, $R^{27}$, $R^{28}$ and $R^{29}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, naphthyl, or biphenylyl, which may optionally be substituted.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl.

Compounds of the formula X, XI and XII are preferred.

Compounds of the formula X, or XII are even more preferred, wherein $R^1$ and $R^4$ are hydrogen, $R^2$, $R^3$, $R^5$ and $R^6$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, $C_7$-$C_{25}$aralkyl, or a group —$X^2$—$R^{18}$, $R^8$ and $R^9$ are independently of each other H, $C_1$-$C_{18}$alkyl, $C_1$-$C_{18}$alkyl which is interrupted by D, $C_1$-$C_{18}$perfluoroalkyl, $C_6$-$C_{18}$aryl, which may optionally be substituted by $C_1$-$C_{18}$alkyl, $C_{18}$alkoxy, or $C_1$-$C_{18}$alkoxy which is interrupted by D; $C_1$-$C_{18}$alkoxy, $C_1$-$C_{18}$alkoxy which is interrupted by D, or a group —$X^2$—$R^{18}$; or two substituents $R^2$ and $R^3$ and/or $R^5$ and $R^6$, which are adjacent to each other, together form a group

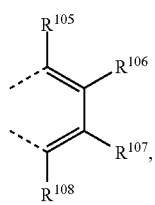

or two substituents $R^5$ and $R^3$, which are adjacent to each other, together form a group

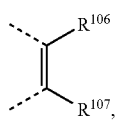

wherein $R^{105}$, $R^{106}$, $R^{107}$ and —$R^{108}$ are independently of each other H, or $C_1$-$C_8$alkyl, or $R^8$ and $R^9$ together form a group

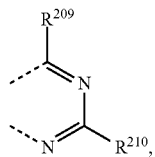

wherein $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$— $R^{18}$, wherein $X^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$—;

D is —CO—; —COO—; —S—; —SO—; —$SO_2$—; —O—; —$NR^{25}$—; —$CR^{23}$=$CR^{24}$—; or —C≡C—; wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or $R^{25}$ and $R^{26}$ together form a five or six membered ring.

In a further preferred embodiment the present invention relates to compounds of formula

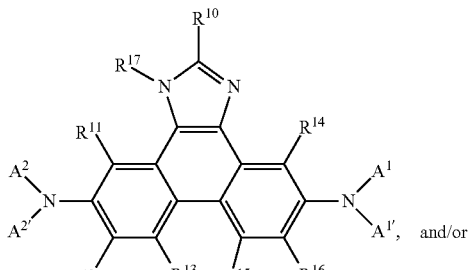

(XIIa)

and/or

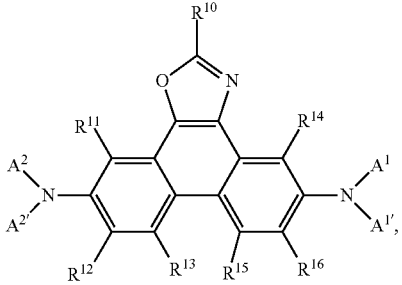

(XIIb)

wherein $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$— $R^{18}$, wherein $X^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$—;

$R^{11}$ and $R^{14}$ are hydrogen, $R^{12}$, $R^{13}$, $R^{15}$ and $R^{16}$ are hydrogen, $R^{17}$ is $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—; or two substituents $R^5$ and $R^3$, $R^{12}$ and $R^{13}$, and/or $R^{15}$ and $R^{16}$, which are adjacent to each other, together form a group

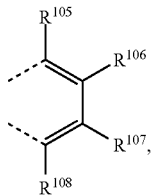

or two substituents $R^{15}$ and $R^{13}$, which are adjacent to each other, together form a group

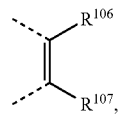

wherein $R^{105}$, $R^{106}$, $R^{107}$ and $R^{108}$ are independently of each other H, or $C_1$-$C_8$alkyl, D is —S—; —O—; or —NR$^{25}$—;

E is —OR$^{29}$; —SR$^{29}$; —NR$^{25}$R$^{26}$; —CN; or F; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{25}$ and $R^{26}$ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or $R^{25}$ and $R^{26}$ together form a five or six membered ring, in particular

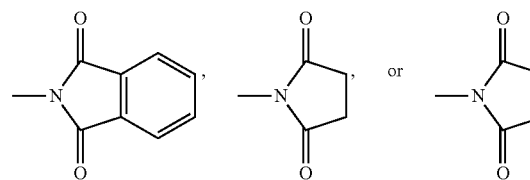

and $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

In a preferred embodiment the present invention is directed to an EL device comprising compounds of formula

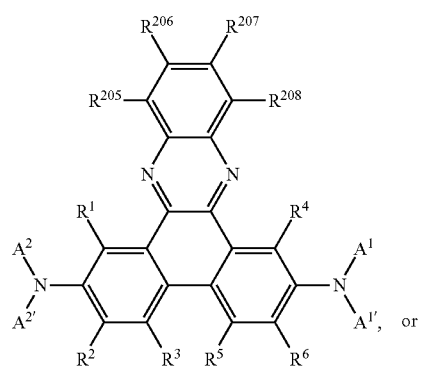

(Xa)

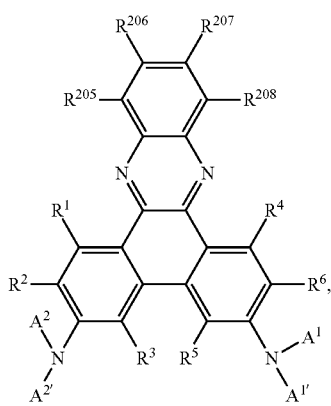

(XVIa)

wherein $R^1$, $R^2$, $R^3$, $R^4$, $R^5$, $R^6$, $A^1$, $A^{1'}$, $A^2$, $A^{2'}$, $R^{205}$, $R^{206}$, $R^{207}$, and $R^{208}$ are as defined above.

In an especially preferred embodiment the present invention is directed to an EL device comprising compounds of formula

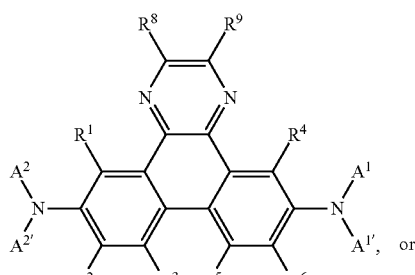

(Xb)

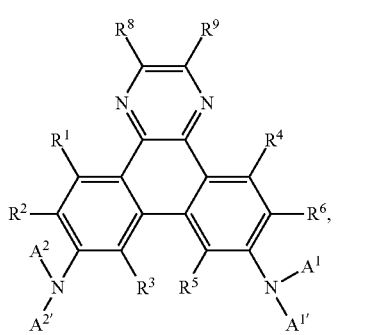

(XVIb)

wherein $R^1$, $R^2$, $R^3$, $R^4$, $R^5$, $R^6$, $A^1$, $A^{1'}$, $A^2$, $A^{2'}$, $R^8$ and $R^9$ are as defined above.

$A^1$, $A^2$, $A^{1'}$ and $A^{2'}$ are independently of each other especially phenyl, naphthyl, anthryl, biphenylyl, 2-fluorenyl, phenanthryl, or perylenyl, which can optionally be substituted, such as

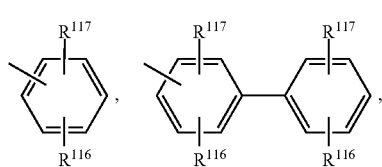

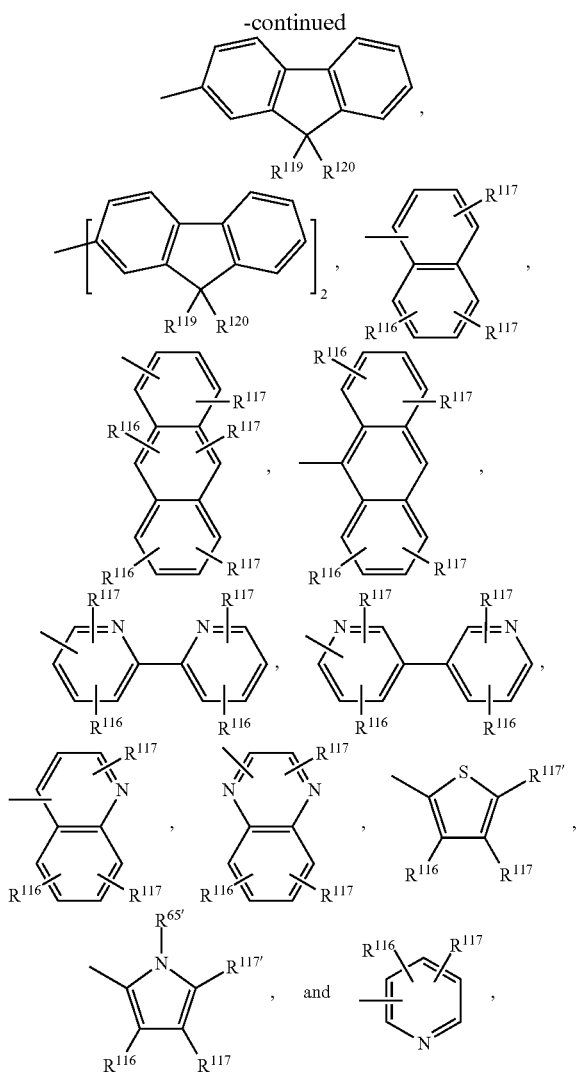

or A¹ and A¹' or A² and A²' together with the nitrogen atom to which they are bonded form a heteroaromatic ring, or ring system, such as

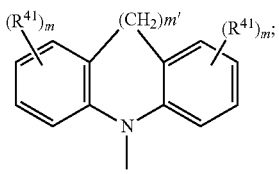

m' is 0, 1, or 2;

m can be the same or different at each occurrence and is 0, 1, 2, or 3, especially 0, 1, or 2, very especially 0 or 1;

$R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is H, a $C_1$-$C_{25}$alkyl group, or a $C_4$-$C_{18}$cycloalkyl group, $R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —$SO_2$—, —O—, —$NR^{65}$—, —Si$R^{70}R^{71}$—, —$POR^{72}$—, —$CR^{63}$=$CR^{64}$—, or —C≡C—, and E is —$OR^{69}$, —$SR^{69}$, —$NR^{65}R^{66}$, —$COR^{68}$, —$COOR^{67}$, —$CONR^{65}R^{66}$, —CN, or halogen, G is E, or $C_1$-$C_{18}$alkyl, $R^{63}$, $R^{64}$, $R^{65}$ and $R^{66}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ and $R^{68}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is H; $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl; or $A^1$, $A^2$, $A^{1'}$ and $A^{2'}$ are independently of each other a group

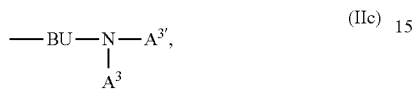

wherein BU is

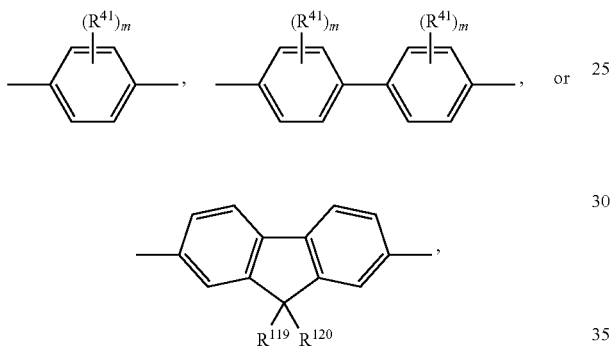

wherein $R^{41}$ and m are as defined above.

Examples of

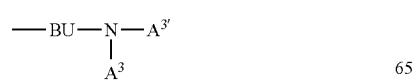

are shown below:

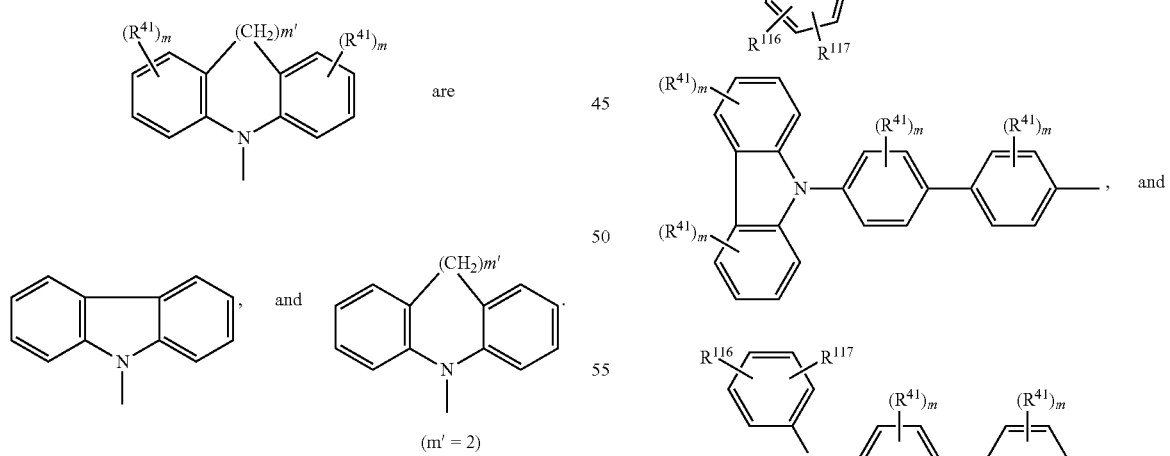

wherein $R^{41}$, $R^{116}$, $R^{117}$, $R^{119}$, $R^{120}$ and m are as defined above.

Compounds of the formula

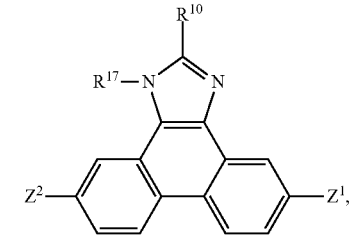

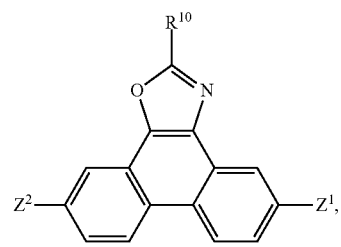

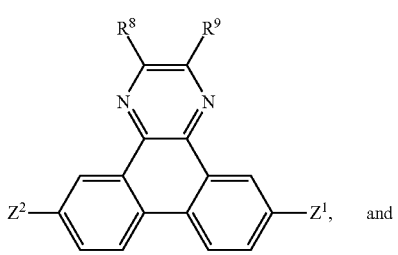

and

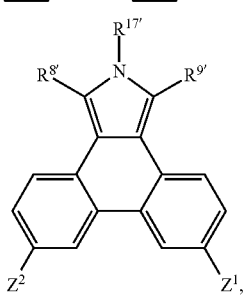

are preferred, wherein $R^8$ and $R^9$ are independently of each other

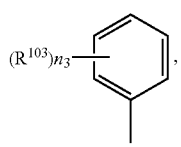, 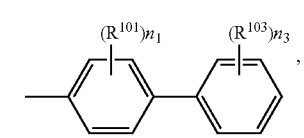,

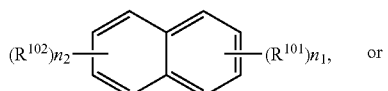 or

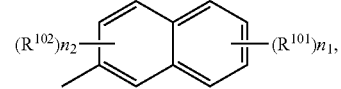

$R^{17}$ is $R^8$, or a group

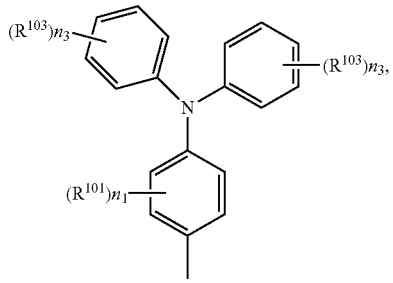

$R^{10}$ is $R^8$, or a group

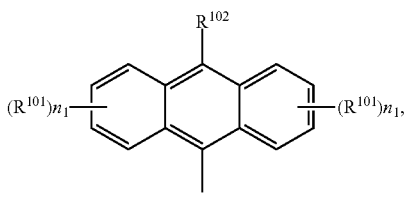

$R^{17'}$ is $R^{17}$, or a group

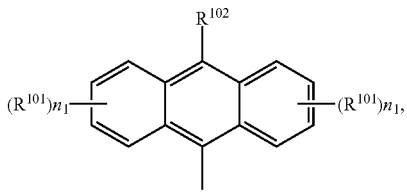

wherein $n_1$ is 0, or an integer 1, 2, 3, or 4, $n_2$ is 0, or an integer 1, 2, or 3, $n_3$ is 0, or an integer 1, 2, 3, 4, or 5, $R^{101}$, $R^{102}$ and $R^{103}$ are independently of each other $C_1$-$C_{25}$alkyl, which may optionally be interrupted by —O—, or $C_1$-$C_{25}$alkoxy;

$Z^1$ and $Z^2$ are as defined above and are preferably independently of each other

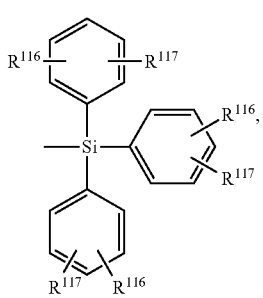 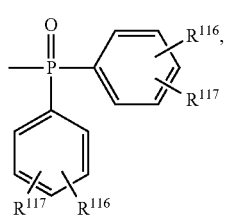

very especially a group of formula

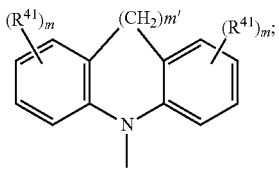

m' is 0, 1, or 2, —NA¹A¹', or a group

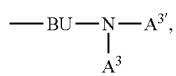

wherein $A^1$, $A^{1'}$, $A^3$ and $A^{3'}$ are independently of each other

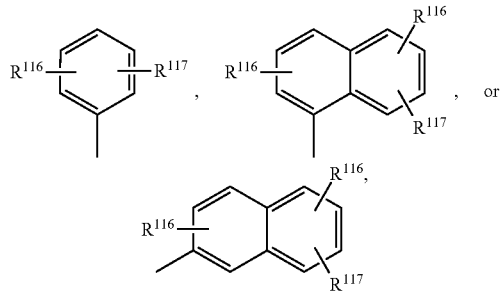

$R^{116}$ and $R^{117}$ are independently of each other $C_1$-$C_{25}$alkyl, which may optionally be interrupted by —O—, or $C_1$-$C_{25}$alkoxy;

Bu is

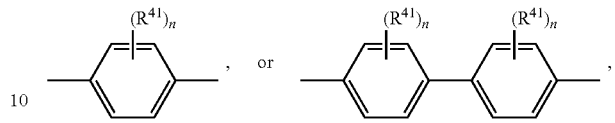

wherein $R^{41}$ can be the same or different at each occurrence and is $C_1$-$C_{25}$alkyl, which may optionally be interrupted by —O—, or $C_1$-$C_{25}$alkoxy; n is 0, 1, or 2.

In another embodiment of the present invention EL devices are preferred, comprising compounds of formula

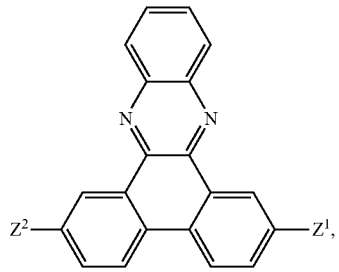

wherein $Z^1$ and $Z^2$ are as defined above.

Examples of particularly preferred compounds are shown below:

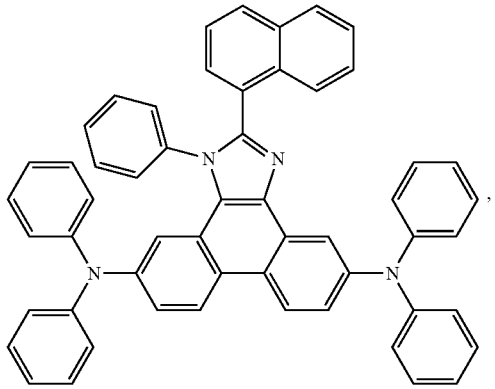

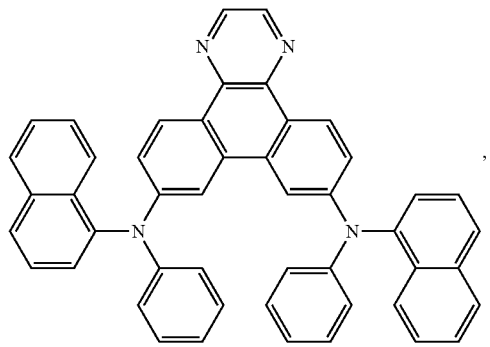

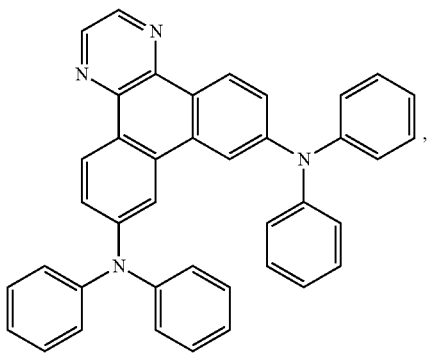

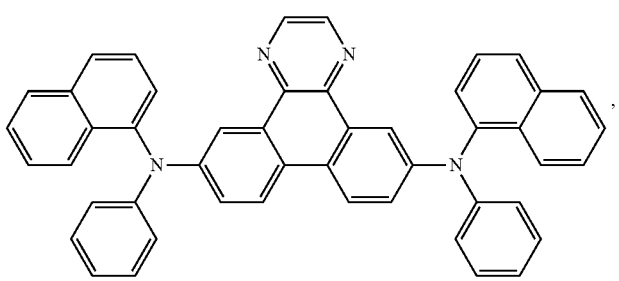

-continued
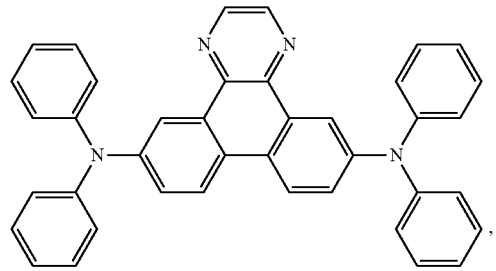
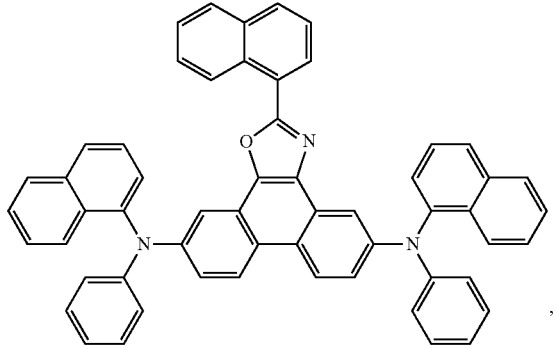
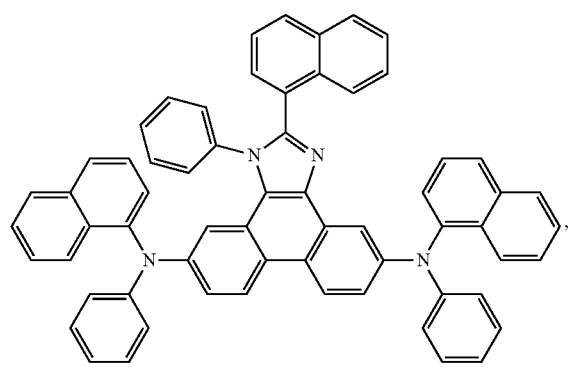
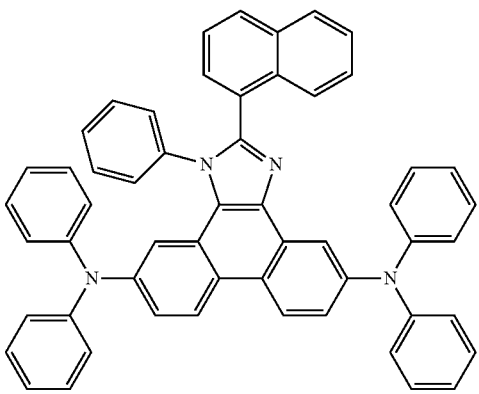
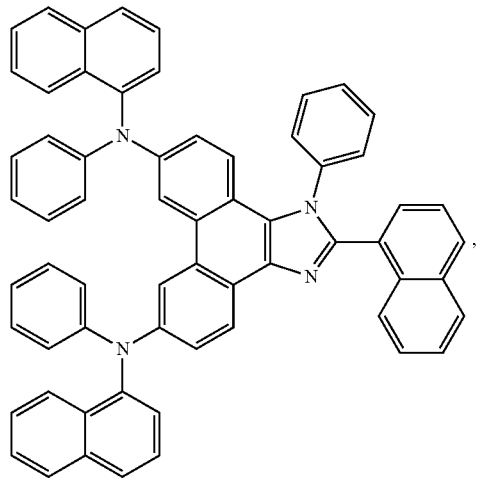
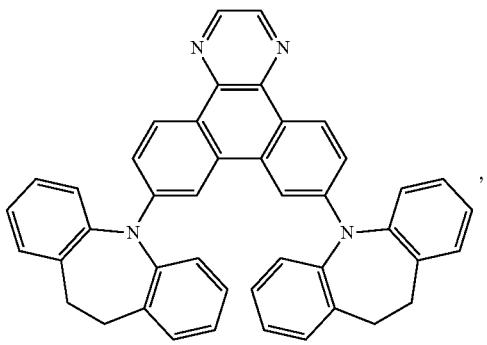
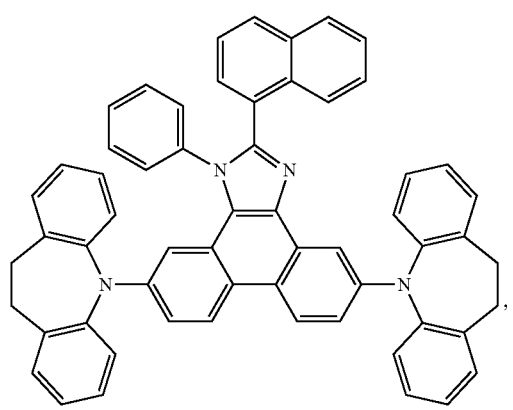

-continued
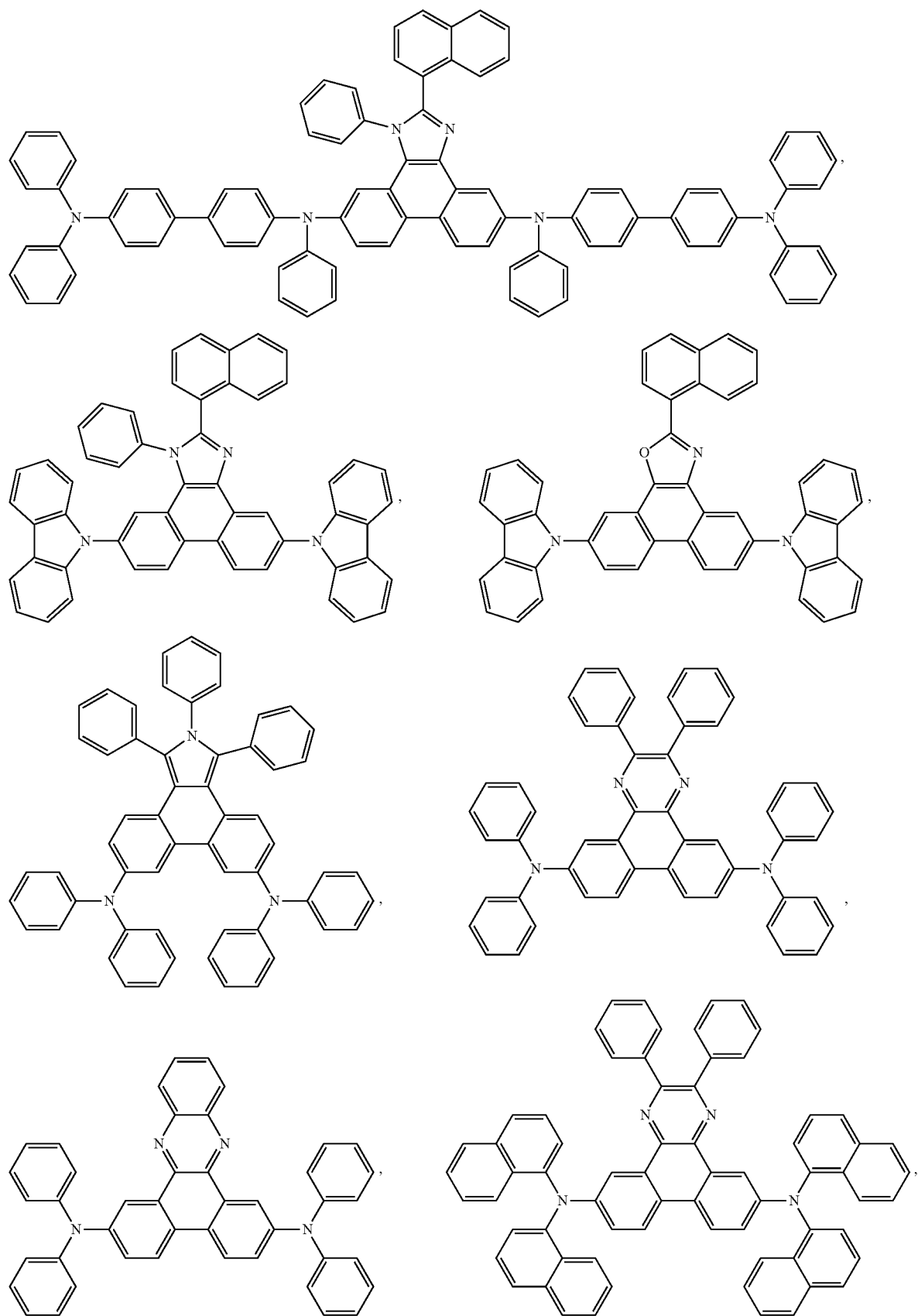

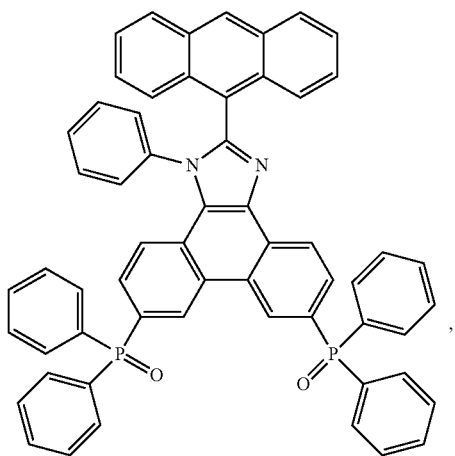
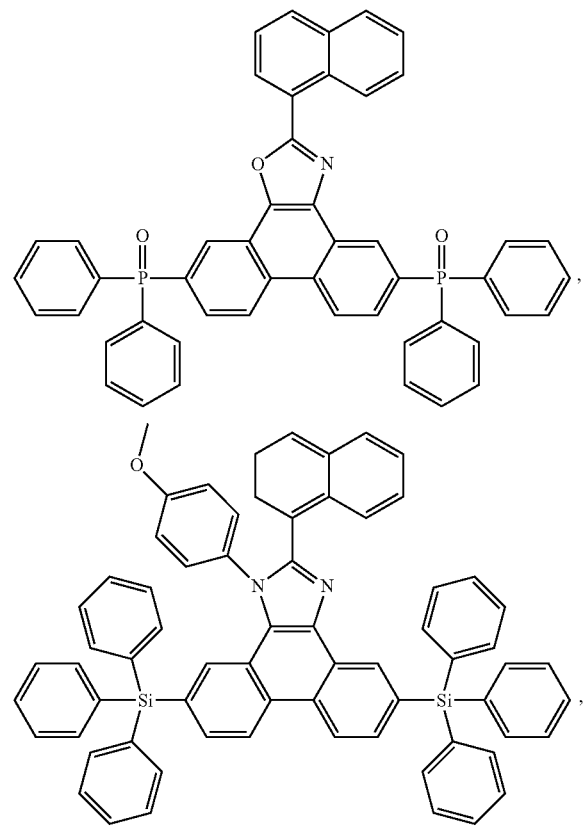
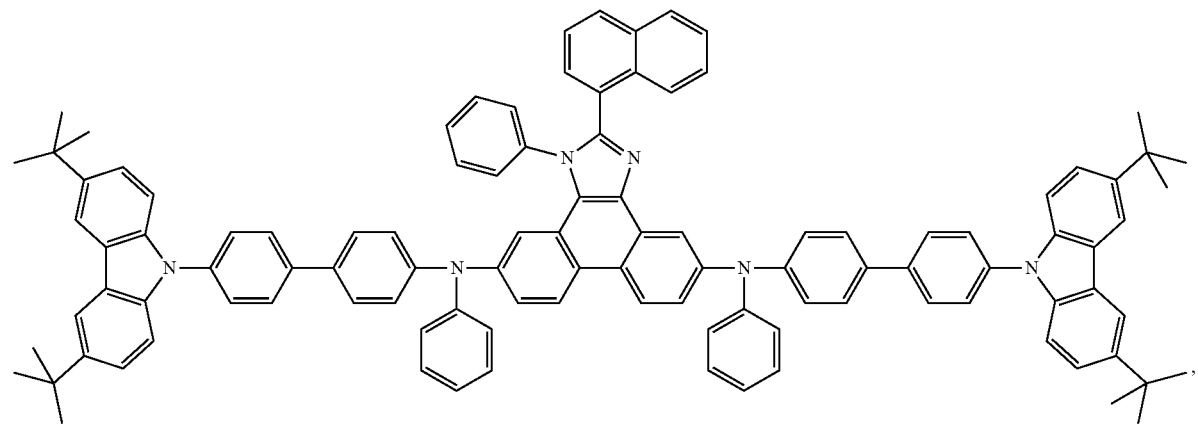
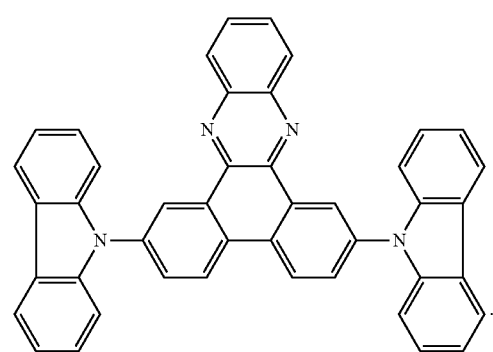
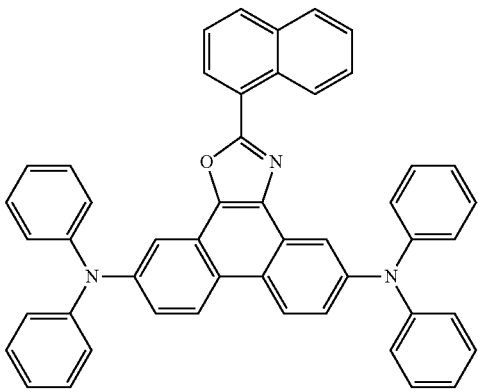

35
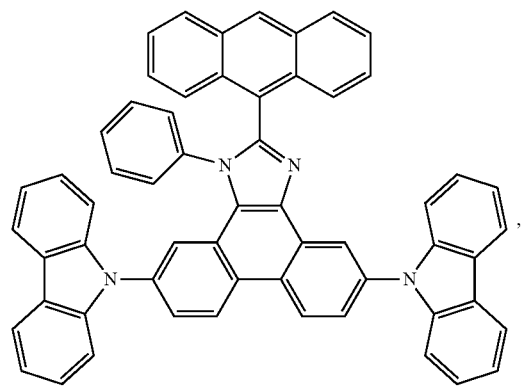
36
-continued
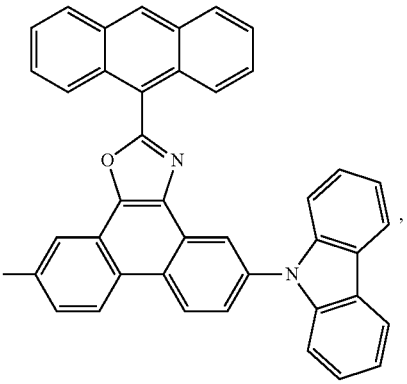
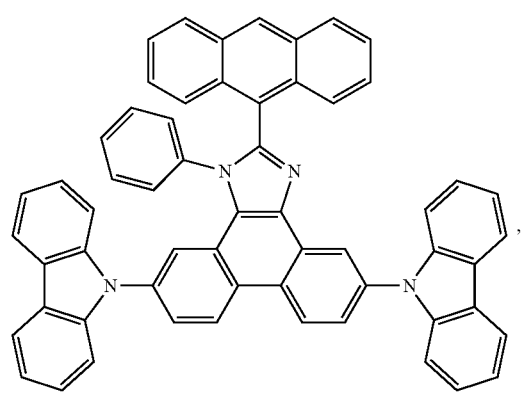
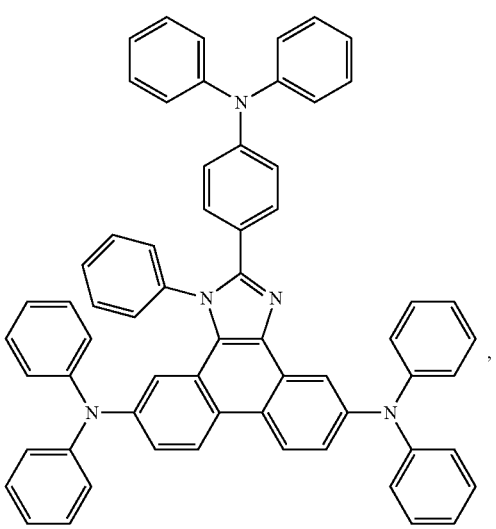
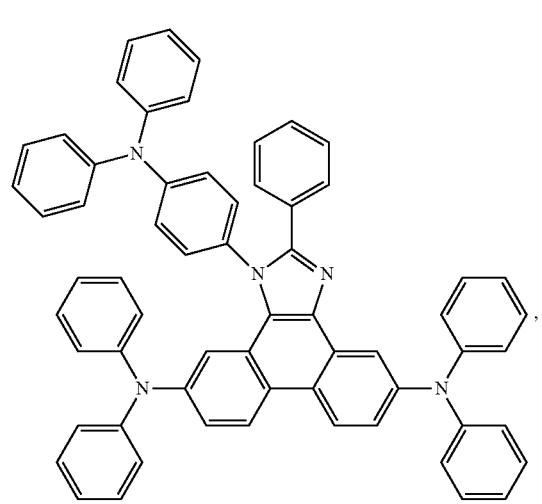
or
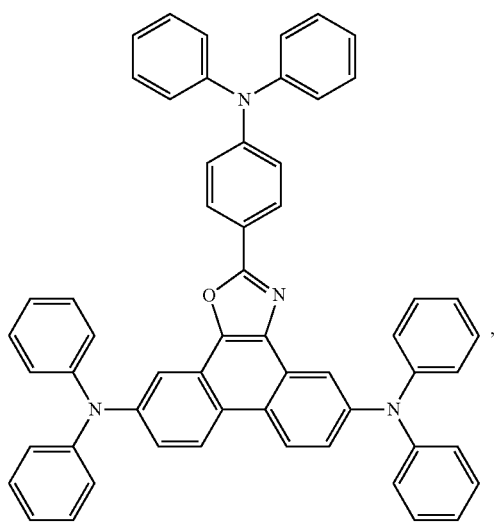

The compounds of the formula I, wherein $Z^1$ and $Z^2$ are independently of each other —$NA^1A^{1'}$, or

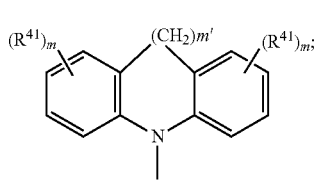

can, for example, be prepared according to a process, which comprises reacting a compound of formula

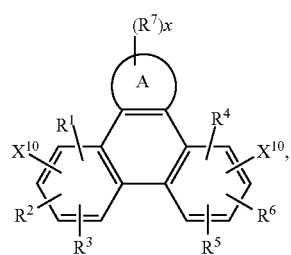

(XX)

wherein $X^{10}$ stands for halogen, such as bromo or iodo, preferably iodo, with a compound of formula $HNA^1A^{1'}$, or

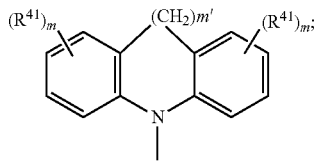

in the presence of a base, such as sodium hydride, potassium carbonate, or sodium carbonate, and a catalyst, such as copper (0) or copper (I) (such as copper, copper-bronze, copper bromide iodide, or copper bromide) in a solvent, such as toluene, dimethyl formamide, or dimethyl sulfoxide, wherein $R^7$, x, m', A, $A^1$, $A^{1'}$, $R^1$, $R^2$, $R^3$, $R^4$, $R^5$, $R^6$, $R^{41}$ and m are as defined above. This reaction, referred to as an Ullmann condensation, is described by Yamamoto & Kurata, Chem. and Industry, 737-738 (1981), J. Mater. Chem. 14 (2004) 2516, H. B. Goodbrand et al., J. Org. Chem. 64 (1999) 670 and k. D. Belfield et al., J. Org. Chem. 65 (2000) 4475 using copper as catalyst. Additionally palladium catalysts can be used for the coupling of aryl halogen compounds with amines, as described in M. D. Charles et al., Organic Lett. 7 (2005) 3965, A. F. Littke et. al., Angew. Chem. Int. Ed. 41 (2002) 4176 and literature cited therein.

The compounds of formula XX are known from WO06/097419, or PCT/EP2007/056702, or can be prepared according, or in analogy to the methods described therein.

The compounds, wherein $Z^1$ and $Z^2$ are a group

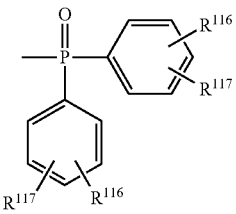

can be prepared according to P. A. Vecchi et al., Org. Lett. 8 (2006) 4211-4214.

The compounds, wherein $Z^1$ and $Z^2$ are a group

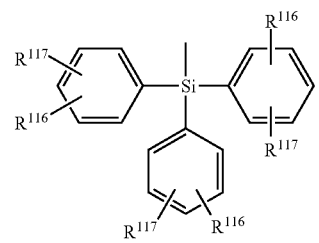

can be prepared according to example IV of US2005/0175857.

Halogen is fluorine, chlorine, bromine and iodine.

$C_1$-$C_{25}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The terms "haloalkyl, haloalkenyl and haloalkynyl" mean groups given by partially or wholly substituting the above-mentioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

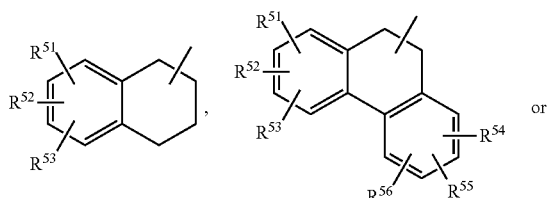

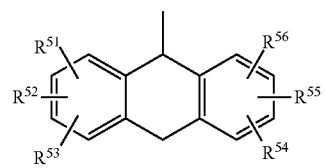

in particular

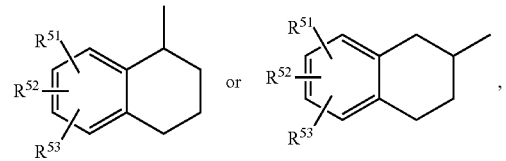

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diaryl groups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Examples of a five or six membered ring formed by, for example, $R^{25}$ and $R^{26}$, respectively are heterocycloalkanes or heterocycloalkenes having from 3 to 5 carbon atoms which can have one additional hetero atom selected from nitrogen, oxygen and sulfur, for example

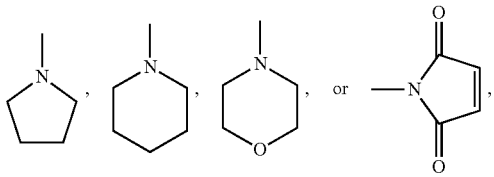

which can be part of a bicyclic system, for example

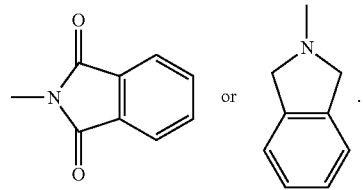

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

If a substituent, such as, for example $R^7$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(O$R^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR^z$, $CH(CH_3)$COO$R^z$, $C(CH_3)_2$COO$R^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)$$CH_2$—O—CO—C($CH_3$)=$CH_2$.

Preferred arylene radicals are 1,4-phenylene, 2,5-tolylene, 1,4-naphthylene, 1,9 antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

The compounds of formula I can be used in organic light emitting diodes (OLEDs), especially as hosts for phosphorescent compounds. Accordingly, the present invention also relates to an electroluminescent device, comprising a compound of formula I. In a preferred embodiment the electroluminescent device comprising a cathode, an anode, and therebetween a light emitting layer containing a host material and a phosphorescent light-emitting material wherein the host material is a compound of formula I.

Suitably, the light-emitting layer of the OLED device comprises a host material and one or more guest materials for emitting light. At least one of the host materials is a compound comprising a compound of formula I. The light-emitting guest material(s) is usually present in an amount less than the amount of host materials and is typically present in an amount of up to 15 wt % of the host, more typically from 0.1 to 10 wt % of the host, and commonly from 2 to 8% of the host. For convenience, the phosphorescent complex guest material may be referred to herein as a phosphorescent material. The emissive layer may comprise a single material, that combines transport and emissive properties. Whether the emissive material is a dopant or a major constituent, emissive layer may comprise other materials, such as dopants that tune the emission of the emissive layer. The emissive layer may include a plurality of emissive materials capable of, in combination, emitting a desired spectrum of light.

Other Host Materials for Phosphorescent Materials

The host material useful in the invention may be used alone or in combination with other host materials. Other host materials should be selected so that the triplet exciton can be transferred efficiently from the host material to the phosphorescent material. Suitable host materials are described in WO00/70655; 01/39234; 01/93642; 02/074015; 02/15645, and US20020117662. Suitable hosts include certain aryl amines, triazoles, indoles and carbazole compounds. Examples of hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665 and US2002/0121638.

The emission wavelengths of cyclometallated Ir(III) complexes of the type IrL$_3$ and IrL$_2$L', such as the green-emitting fac-tris(2-phenylpyridinato-N,C$^{2'}$)iridium(III) and bis(2- phenylpyridinato-N,$C^{2'}$) Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N, $C^{3'}$)iridium(EI)(acetylacetonate) and tris(1-phenylisoquinolinato-N,C)iridium(III). A blue-emitting example is bis(2-(4,6-diflourophenyl)-pyridinato-N,$C^{2'}$)Iridium(III) (picolinate).

Red electrophosphorescence has been reported, using bis(2-(2'-benzo[4,5-a]thienyl)pyridinato-N, $C^3$)iridium (acetylacetonate)[Btp$_2$Ir(acac)] as the phosphorescent material (Adachi, C., Lamansky, S., Baldo, M. A., Kwong, R. C., Thompson, M. E., and Forrest, S. R., App. Phys. Lett., 78, 1622 1624 (2001).

Other important phosphorescent materials include cyclometallated Pt(II) complexes such as cis-bis(2-phenylpyridinato-N,$C^{2'}$)platinum(II), cis-bis(2-(2'-thienyl)pyridinato-N, $C^{3'}$) platinum(II), cis-bis(2-(2'-thienyl)quinolinato-N,$C^{5'}$) platinum(II), or (2-(4,6-diflourophenyl)pyridinato-NC2') platinum(II)acetylacetonate. Pt(II)porphyrin complexes such as 2,3,7,8,12,13,17,18-octaethyl-21H, 23H-porphine platinum(H) are also useful phosphorescent materials.

Still other examples of useful phosphorescent materials include coordination complexes of the trivalent lanthanides such as $Th^{3+}$ and $Eu^{3+}$ (J. Kido et al, Appl. Phys. Lett., 65, 2124 (1994)).

Other important phosphorescent materials are described in WO06/000544 and European patent application no. 07102949.0.

Examples of phosphorescent materials are compounds A-1 to B-234, B-1 to B-234, C-1 to C-44 and D-1 to D-234, which are described in European patent application no. 07102949.0:

| Cpd. | $R^2$ | $R^3$ | $R^6$ |
|---|---|---|---|
| A-1 | H | H | H |
| A-2 | H | H | $OCH_3$ |
| A-3 | H | H | $OCH_2CH_3$ |
| A-4 | H | H | O-n-butyl |
| A-5 | H | H | O-iso-butyl |
| A-6 | H | H | O-2-butyl |
| A-7 | H | H | O-2-ethylhexyl |
| A-8 | H | H | $N(CH_3)_2$ |
| A-9 | H | H | $NPh_2$ |
| A-10 | H | $CF_3$ | H |
| A-11 | $CF_3$ | H | H |
| A-12 | H | $CF_3$ | $OCH_3$ |
| A-13 | $CF_3$ | H | $OCH_3$ |
| A-14 | H | $CF_3$ | $OCH_2CH_3$ |
| A-15 | $CF_3$ | H | $OCH_2CH_3$ |
| A-16 | H | $CF_3$ | O-n-butyl |
| A-17 | $CF_3$ | H | O-n-butyl |
| A-18 | H | $CF_3$ | O-iso-butyl |
| A-19 | $CF_3$ | H | O-iso-butyl |
| A-20 | H | $CF_3$ | O-2-butyl |
| A-21 | $CF_3$ | H | O-2-butyl |
| A-22 | H | $CF_3$ | O-2-ethylhexyl |
| A-23 | $CF_3$ | H | O-2-ethylhexyl |
| A-24 | H | $CF_3$ | $N(CH_3)_2$ |
| A-25 | $CF_3$ | H | $N(CH_3)_2$ |
| A-26 | H | $CF_3$ | $NPh_2$ |
| A-27 | $CF_3$ | H | $NPh_2$ |
| A-28 | H | CN | H |
| A-29 | CN | H | H |
| A-30 | H | CN | $OCH_3$ |
| A-31 | CN | H | $OCH_2CH_3$ |
| A-32 | H | CN | $OCH_2CH_3$ |
| A-33 | CN | H | O-n-butyl |
| A-34 | H | CN | O-n-butyl |
| A-35 | CN | H | O-iso-butyl |
| A-36 | H | CN | O-iso-butyl |
| A-37 | CN | H | O-2-butyl |
| A-38 | H | CN | O-2-butyl |
| A-39 | CN | H | O-2-ethylhexyl |
| A-40 | H | CN | O-2-ethylhexyl |
| A-41 | CN | H | $N(CH_3)_2$ |
| A-42 | H | CN | $N(CH_3)_2$ |
| A-43 | CN | H | $NPh_2$ |
| A-44 | H | CN | $NPh_2$ |

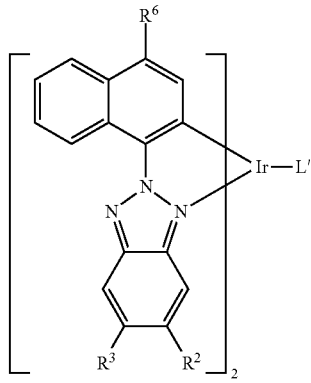

| Cpd. | L' | $R^2$ | $R^3$ | $R^6$ |
|---|---|---|---|---|
| B-1 | $A^{1)}$ | H | H | H |
| B-2 | $A^{1)}$ | H | H | $OCH_3$ |
| B-3 | $A^{1)}$ | H | H | $OCH_2CH_3$ |
| B-4 | $A^{1)}$ | H | H | O-n-butyl |
| B-5 | $A^{1)}$ | H | H | O-iso-butyl |
| B-6 | $A^{1)}$ | H | H | O-2-butyl |
| B-7 | $A^{1)}$ | H | H | O-2-ethylhexyl |
| B-8 | $A^{1)}$ | H | H | $N(CH_3)_2$ |
| B-9 | $A^{1)}$ | H | H | $NPh_2$ |
| B-10 | $A^{1)}$ | H | $CF_3$ | H |
| B-11 | $A^{1)}$ | $CF_3$ | H | H |
| B-12 | $A^{1)}$ | H | $CF_3$ | $OCH_3$ |
| B-13 | $A^{1)}$ | $CF_3$ | H | $OCH_3$ |
| B-14 | $A^{1)}$ | H | $CF_3$ | $OCH_2CH_3$ |
| B-15 | $A^{1)}$ | $CF_3$ | H | $OCH_2CH_3$ |
| B-16 | $A^{1)}$ | H | $CF_3$ | O-n-butyl |
| B-17 | $A^{1)}$ | $CF_3$ | H | O-n-butyl |
| B-18 | $A^{1)}$ | H | $CF_3$ | O-iso-butyl |
| B-19 | $A^{1)}$ | $CF_3$ | H | O-iso-butyl |
| B-20 | $A^{1)}$ | H | $CF_3$ | O-2-butyl |
| B-21 | $A^{1)}$ | $CF_3$ | H | O-2-butyl |
| B-22 | $A^{1)}$ | H | $CF_3$ | O-2-ethylhexyl |
| B-23 | $A^{1)}$ | $CF_3$ | H | O-2-ethylhexyl |
| B-24 | $A^{1)}$ | H | $CF_3$ | $N(CH_3)_2$ |
| B-25 | $A^{1)}$ | $CF_3$ | H | $N(CH_3)_2$ |
| B-26 | $A^{1)}$ | H | $CF_3$ | $NPh_2$ |
| B-27 | $A^{1)}$ | $CF_3$ | H | $NPh_2$ |
| B-28 | $A^{1)}$ | H | CN | H |

-continued

| | | | | |
|---|---|---|---|---|
| B-29 | A[1] | CN | H | H |
| B-30 | A[1] | CN | H | OCH$_3$ |
| B-31 | A[1] | H | CN | OCH$_3$ |
| B-32 | A[1] | CN | H | OCH$_2$CH$_3$ |
| B-33 | A[1] | H | CN | OCH$_2$CH$_3$ |
| B-34 | A[1] | CN | H | O-n-butyl |
| B-35 | A[1] | H | CN | O-n-butyl |
| B-36 | A[1] | CN | H | O-iso-butyl |
| B-37 | A[1] | H | CN | O-iso-butyl |
| B-38 | A[1] | CN | H | O-2-butyl |
| B-39 | A[1] | H | CN | O-2-butyl |
| B-40 | A[1] | CN | H | O-2-ethylhexyl |
| B-41 | A[1] | H | CN | O-2-ethylhexyl |
| B-42 | A[1] | CN | H | N(CH$_3$)$_2$ |
| B-43 | A[1] | H | CN | N(CH$_3$)$_2$ |
| B-44 | A[1] | CN | H | NPh$_2$ |
| B-45 | A[1] | H | CN | NPh$_2$ |
| B-46 | B[1] | H | H | H |
| B-47 | B[1] | H | H | OCH$_3$ |
| B-48 | B[1] | H | H | OCH$_2$CH$_3$ |
| B-49 | B[1] | H | H | O-n-butyl |
| B-50 | B[1] | H | H | O-iso-butyl |
| B-51 | B[1] | H | H | O-2-butyl |
| B-52 | B[1] | H | H | O-2-ethylhexyl |
| B-53 | B[1] | H | H | N(CH$_3$)$_2$ |
| B-54 | B[1] | H | H | NPh$_2$ |
| B-55 | B[1] | H | CF$_3$ | H |
| B-56 | B[1] | CF$_3$ | H | H |
| B-57 | B[1] | H | CF$_3$ | OCH$_3$ |
| B-58 | B[1] | CF$_3$ | H | OCH$_3$ |
| B-59 | B[1] | H | CF$_3$ | OCH$_2$CH$_3$ |
| B-60 | B[1] | CF$_3$ | H | OCH$_2$CH$_3$ |
| B-61 | B[1] | H | CF$_3$ | O-n-butyl |
| B-62 | B[1] | CF$_3$ | H | O-n-butyl |
| B-63 | B[1] | H | CF$_3$ | O-iso-butyl |
| B-64 | B[1] | CF$_3$ | H | O-iso-butyl |
| B-65 | B[1] | H | CF$_3$ | O-2-butyl |
| B-66 | B[1] | CF$_3$ | H | O-2-butyl |
| B-67 | B[1] | H | CF$_3$ | O-2-ethylhexyl |
| B-68 | B[1] | CF$_3$ | H | O-2-ethylhexyl |
| B-69 | B[1] | H | CF$_3$ | N(CH$_3$)$_2$ |
| B-70 | B[1] | CF$_3$ | H | N(CH$_3$)$_2$ |
| B-71 | B[1] | H | CF$_3$ | NPh$_2$ |
| B-72 | B[1] | CF$_3$ | H | NPh$_2$ |
| B-73 | B[1] | H | CN | H |
| B-74 | B[1] | CN | H | H |
| B-75 | B[1] | CN | H | OCH$_3$ |
| B-76 | B[1] | H | CN | OCH$_3$ |
| B-77 | B[1] | CN | H | OCH$_2$CH$_3$ |
| B-78 | B[1] | H | CN | OCH$_2$CH$_3$ |
| B-79 | B[1] | CN | H | O-n-butyl |
| B-80 | B[1] | H | CN | O-n-butyl |
| B-81 | B[1] | CN | H | O-iso-butyl |
| B-82 | B[1] | H | CN | O-iso-butyl |
| B-83 | B[1] | CN | H | O-2-butyl |
| B-84 | B[1] | H | CN | O-2-butyl |
| B-85 | B[1] | CN | H | O-2-ethylhexyl |
| B-86 | B[1] | H | CN | O-2-ethylhexyl |
| B-87 | B[1] | CN | H | N(CH$_3$)$_2$ |
| B-88 | B[1] | H | CN | N(CH$_3$)$_2$ |
| B-89 | B[1] | CN | H | NPh$_2$ |
| B-99 | B[1] | H | CN | NPh$_2$ |
| B-100 | C[1] | H | H | H |
| B-101 | C[1] | H | H | OCH$_3$ |
| B-102 | C[1] | H | H | OCH$_2$CH$_3$ |
| B-103 | C[1] | H | H | O-n-butyl |
| B-104 | C[1] | H | H | O-iso-butyl |
| B-105 | C[1] | H | H | O-2-butyl |
| B-106 | C[1] | H | H | O-2-ethylhexyl |
| B-107 | C[1] | H | H | N(CH$_3$)$_2$ |
| B-108 | C[1] | H | H | NPh$_2$ |
| B-109 | C[1] | H | CF$_3$ | H |
| B-110 | C[1] | CF$_3$ | H | H |
| B-111 | C[1] | H | CF$_3$ | OCH$_3$ |
| B-112 | C[1] | CF$_3$ | H | OCH$_3$ |
| B-113 | C[1] | H | CF$_3$ | OCH$_2$CH$_3$ |
| B-114 | C[1] | CF$_3$ | H | OCH$_2$CH$_3$ |
| B-115 | C[1] | H | CF$_3$ | O-n-butyl |
| B-116 | C[1] | CF$_3$ | H | O-n-butyl |
| B-117 | C[1] | H | CF$_3$ | O-iso-butyl |
| B-118 | C[1] | CF$_3$ | H | O-iso-butyl |
| B-119 | C[1] | H | CF$_3$ | O-2-butyl |
| B-120 | C[1] | CF$_3$ | H | O-2-butyl |
| B-121 | C[1] | H | CF$_3$ | O-2-ethylhexyl |
| B-122 | C[1] | CF$_3$ | H | O-2-ethylhexyl |
| B-123 | C[1] | H | CF$_3$ | N(CH$_3$)$_2$ |
| B-124 | C[1] | CF$_3$ | H | N(CH$_3$)$_2$ |
| B-125 | C[1] | H | CF$_3$ | NPh$_2$ |
| B-126 | C[1] | CF$_3$ | H | NPh$_2$ |
| B-127 | C[1] | H | CN | H |
| B-128 | C[1] | CN | H | H |
| B-129 | C[1] | CN | H | OCH$_3$ |
| B-130 | C[1] | H | CN | OCH$_3$ |
| B-131 | C[1] | CN | H | OCH$_2$CH$_3$ |
| B-132 | C[1] | H | CN | OCH$_2$CH$_3$ |
| B-133 | C[1] | CN | H | O-n-butyl |
| B-134 | C[1] | H | CN | O-n-butyl |
| B-135 | C[1] | CN | H | O-iso-butyl |
| B-136 | C[1] | H | CN | O-iso-butyl |
| B-137 | C[1] | CN | H | O-2-butyl |
| B-138 | C[1] | H | CN | O-2-butyl |
| B-139 | C[1] | CN | H | O-2-ethylhexyl |
| B-140 | C[1] | H | CN | O-2-ethylhexyl |
| B-141 | C[1] | CN | H | N(CH$_3$)$_2$ |
| B-142 | C[1] | H | CN | N(CH$_3$)$_2$ |
| B-143 | C[1] | H | CN | NPh$_2$ |
| B-144 | C[1] | CN | H | NPh$_2$ |
| B-145 | D[1] | H | H | H |
| B-146 | D[1] | H | H | OCH$_3$ |
| B-147 | D[1] | H | H | OCH$_2$CH$_3$ |
| B-148 | D[1] | H | H | O-n-butyl |
| B-149 | D[1] | H | H | O-iso-butyl |
| B-150 | D[1] | H | H | O-2-butyl |
| B-151 | D[1] | H | H | O-2-ethylhexyl |
| B-152 | D[1] | H | H | N(CH$_3$)$_2$ |
| B-153 | D[1] | H | H | NPh$_2$ |
| B-154 | D[1] | H | CF$_3$ | H |
| B-155 | D[1] | CF$_3$ | H | H |
| B-156 | D[1] | H | CF$_3$ | OCH$_3$ |
| B-157 | D[1] | CF$_3$ | H | OCH$_3$ |
| B-158 | D[1] | H | CF$_3$ | OCH$_2$CH$_3$ |
| B-159 | D[1] | CF$_3$ | H | OCH$_2$CH$_3$ |
| B-160 | D[1] | H | CF$_3$ | O-n-butyl |
| B-161 | D[1] | CF$_3$ | H | O-n-butyl |
| B-162 | D[1] | H | CF$_3$ | O-iso-butyl |
| B-163 | D[1] | CF$_3$ | H | O-iso-butyl |
| B-164 | D[1] | H | CF$_3$ | O-2-butyl |
| B-165 | D[1] | CF$_3$ | H | O-2-butyl |
| B-166 | D[1] | H | CF$_3$ | O-2-ethylhexyl |
| B-167 | D[1] | CF$_3$ | H | O-2-ethylhexyl |
| B-168 | D[1] | H | CF$_3$ | N(CH$_3$)$_2$ |
| B-169 | D[1] | CF$_3$ | H | N(CH$_3$)$_2$ |
| B-170 | D[1] | H | CF$_3$ | NPh$_2$ |
| B-171 | D[1] | CF$_3$ | H | NPh$_2$ |
| B-172 | D[1] | H | CN | H |
| B-173 | D[1] | CN | H | H |
| B-174 | D[1] | CN | H | OCH$_3$ |
| B-175 | D[1] | H | CN | OCH$_3$ |
| B-176 | D[1] | CN | H | OCH$_2$CH$_3$ |
| B-177 | D[1] | H | CN | OCH$_2$CH$_3$ |
| B-178 | D[1] | CN | H | O-n-butyl |
| B-179 | D[1] | H | CN | O-n-butyl |
| B-180 | D[1] | CN | H | O-iso-butyl |
| B-181 | D[1] | H | CN | O-iso-butyl |
| B-182 | D[1] | CN | H | O-2-butyl |
| B-183 | D[1] | H | CN | O-2-butyl |
| B-184 | D[1] | CN | H | O-2-ethylhexyl |
| B-185 | D[1] | H | CN | O-2-ethylhexyl |
| B-186 | D[1] | CN | H | N(CH$_3$)$_2$ |
| B-187 | D[1] | H | CN | N(CH$_3$)$_2$ |
| B-188 | D[1] | CN | H | NPh$_2$ |
| B-189 | D[1] | H | CN | NPh$_2$ |
| B-190 | E[1] | H | H | H |
| B-191 | E[1] | H | H | OCH$_3$ |
| B-192 | E[1] | H | H | OCH$_2$CH$_3$ |
| B-193 | E[1] | H | H | O-n-butyl |
| B-194 | E[1] | H | H | O-iso-butyl |
| B-195 | E[1] | H | H | O-2-butyl |

-continued

| Cpd. | | R² | R³ | R⁶ |
|---|---|---|---|---|
| B-196 | E¹⁾ | H | H | O-2-ethylhexyl |
| B-197 | E¹⁾ | H | H | N(CH₃)₂ |
| B-198 | E¹⁾ | H | H | NPh₂ |
| B-199 | E¹⁾ | H | CF₃ | H |
| B-200 | E¹⁾ | CF₃ | H | H |
| B-201 | E¹⁾ | H | CF₃ | OCH₃ |
| B-202 | E¹⁾ | CF₃ | H | OCH₃ |
| B-203 | E¹⁾ | H | CF₃ | OCH₂CH₃ |
| B-204 | E¹⁾ | CF₃ | H | OCH₂CH₃ |
| B-205 | E¹⁾ | H | CF₃ | O-n-butyl |
| B-206 | E¹⁾ | CF₃ | H | O-n-butyl |
| B-207 | E¹⁾ | H | CF₃ | O-iso-butyl |
| B-208 | E¹⁾ | CF₃ | H | O-iso-butyl |
| B-209 | E¹⁾ | H | CF₃ | O-2-butyl |
| B-210 | E¹⁾ | CF₃ | H | O-2-butyl |
| B-211 | E¹⁾ | H | CF₃ | O-2-ethylhexyl |
| B-212 | E¹⁾ | CF₃ | H | O-2-ethylhexyl |
| B-213 | E¹⁾ | H | CF₃ | N(CH₃)₂ |
| B-214 | E¹⁾ | CF₃ | H | N(CH₃)₂ |
| B-215 | E¹⁾ | H | CF₃ | NPh₂ |
| B-216 | E¹⁾ | CF₃ | H | NPh₂ |
| B-217 | E¹⁾ | H | CN | H |
| B-218 | E¹⁾ | CN | H | H |
| B-219 | E¹⁾ | CN | H | OCH₃ |
| B-220 | E¹⁾ | H | CN | OCH₃ |
| B-221 | E¹⁾ | CN | H | OCH₂CH₃ |
| B-222 | E¹⁾ | H | CN | OCH₂CH₃ |
| B-223 | E¹⁾ | CN | H | O-n-butyl |
| B-224 | E¹⁾ | H | CN | O-n-butyl |
| B-225 | E¹⁾ | CN | H | O-iso-butyl |
| B-226 | E¹⁾ | H | CN | O-iso-butyl |
| B-227 | E¹⁾ | CN | H | O-2-butyl |
| B-228 | E¹⁾ | H | CN | O-2-butyl |
| B-229 | E¹⁾ | CN | H | O-2-ethylhexyl |
| B-230 | E¹⁾ | H | CN | O-2-ethylhexyl |
| B-231 | E¹⁾ | CN | H | N(CH₃)₂ |
| B-232 | E¹⁾ | H | CN | N(CH₃)₂ |
| B-233 | E¹⁾ | CN | H | NPh₂ |
| B-234 | E¹⁾ | H | CN | NPh₂ |

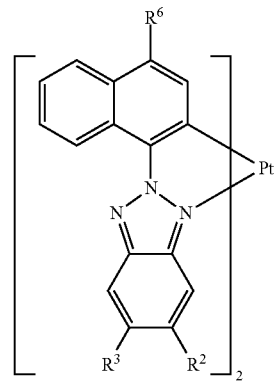

| Cpd. | R² | R³ | R⁶ |
|---|---|---|---|
| C-1 | H | H | H |
| C-2 | H | H | OCH₃ |
| C-3 | H | H | OCH₂CH₃ |
| C-4 | H | H | O-n-butyl |
| C-5 | H | H | O-iso-butyl |
| C-6 | H | H | O-2-butyl |
| C-7 | H | H | O-2-ethylhexyl |
| C-8 | H | H | N(CH₃)₂ |
| C-9 | H | H | NPh₂ |
| C-10 | H | CF₃ | H |
| C-11 | CF₃ | H | H |
| C-12 | H | CF₃ | OCH₃ |
| C-13 | CF₃ | H | OCH₃ |
| C-14 | H | CF₃ | OCH₂CH₃ |
| C-15 | CF₃ | H | OCH₂CH₃ |
| C-16 | H | CF₃ | O-n-butyl |
| C-17 | CF₃ | H | O-n-butyl |
| C-18 | H | CF₃ | O-iso-butyl |
| C-19 | CF₃ | H | O-iso-butyl |
| C-20 | H | CF₃ | O-2-butyl |
| C-21 | CF₃ | H | O-2-butyl |
| C-22 | H | CF₃ | O-2-ethylhexyl |
| C-23 | CF₃ | H | O-2-ethylhexyl |
| C-24 | H | CF₃ | N(CH₃)₂ |
| C-25 | CF₃ | H | N(CH₃)₂ |
| C-26 | H | CF₃ | NPh₂ |
| C-27 | CF₃ | H | NPh₂ |
| C-28 | H | CN | H |
| C-29 | CN | H | H |
| C-30 | H | CN | OCH₃ |
| C-31 | CN | H | OCH₂CH₃ |
| C-32 | H | CN | OCH₂CH₃ |
| C-33 | CN | H | O-n-butyl |
| C-34 | H | CN | O-n-butyl |
| C-35 | CN | H | O-iso-butyl |
| C-36 | H | CN | O-iso-butyl |
| C-37 | CN | H | O-2-butyl |
| C-38 | H | CN | O-2-butyl |
| C-39 | CN | H | O-2-ethylhexyl |
| C-40 | H | CN | O-2-ethylhexyl |
| C-41 | CN | H | N(CH₃)₂ |
| C-42 | H | CN | N(CH₃)₂ |
| C-43 | CN | H | NPh₂ |
| C-44 | H | CN | NPh₂ |

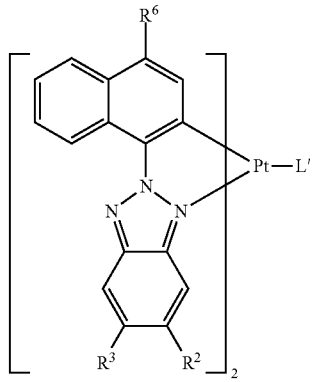

| Cpd. | L' | R² | R³ | R⁶ |
|---|---|---|---|---|
| D-1 | A¹⁾ | H | H | H |
| D-2 | A¹⁾ | H | H | OCH₃ |
| D-3 | A¹⁾ | H | H | OCH₂CH₃ |
| D-4 | A¹⁾ | H | H | O-n-butyl |
| D-5 | A¹⁾ | H | H | O-iso-butyl |
| D-6 | A¹⁾ | H | H | O-2-butyl |
| D-7 | A¹⁾ | H | H | O-2-ethylhexyl |
| D-8 | A¹⁾ | H | H | N(CH₃)₂ |
| D-9 | A¹⁾ | H | H | NPh₂ |
| D-10 | A¹⁾ | H | CF₃ | H |
| D-11 | A¹⁾ | CF₃ | H | H |
| D-12 | A¹⁾ | H | CF₃ | OCH₃ |
| D-13 | A¹⁾ | CF₃ | H | OCH₃ |
| D-14 | A¹⁾ | H | CF₃ | OCH₂CH₃ |
| D-15 | A¹⁾ | CF₃ | H | OCH₂CH₃ |
| D-16 | A¹⁾ | H | CF₃ | O-n-butyl |
| D-17 | A¹⁾ | CF₃ | H | O-n-butyl |
| D-18 | A¹⁾ | H | CF₃ | O-iso-butyl |
| D-19 | A¹⁾ | CF₃ | H | O-iso-butyl |
| D-20 | A¹⁾ | H | CF₃ | O-2-butyl |
| D-21 | A¹⁾ | CF₃ | H | O-2-butyl |
| D-22 | A¹⁾ | H | CF₃ | O-2-ethylhexyl |
| D-23 | A¹⁾ | CF₃ | H | O-2-ethylhexyl |
| D-24 | A¹⁾ | H | CF₃ | N(CH₃)₂ |
| D-25 | A¹⁾ | CF₃ | H | N(CH₃)₂ |
| D-26 | A¹⁾ | H | CF₃ | NPh₂ |
| D-27 | A¹⁾ | CF₃ | H | NPh₂ |
| D-28 | A¹⁾ | H | CN | H |
| D-29 | A¹⁾ | CN | H | H |
| D-30 | A¹⁾ | H | CN | OCH₃ |
| D-31 | A¹⁾ | CN | H | OCH₃ |
| D-32 | A¹⁾ | H | CN | OCH₂CH₃ |
| D-33 | A¹⁾ | CN | H | OCH₂CH₃ |

-continued

| | | | | |
|---|---|---|---|---|
| D-34 | A[1] | CN | H | O-n-butyl |
| D-35 | A[1] | H | CN | O-n-butyl |
| D-36 | A[1] | CN | H | O-iso-butyl |
| D-37 | A[1] | H | CN | O-iso-butyl |
| D-38 | A[1] | CN | H | O-2-butyl |
| D-39 | A[1] | H | CN | O-2-butyl |
| D-40 | A[1] | CN | H | O-2-ethylhexyl |
| D-41 | A[1] | H | CN | O-2-ethylhexyl |
| D-42 | A[1] | CN | H | $N(CH_3)_2$ |
| D-43 | A[1] | H | CN | $N(CH_3)_2$ |
| D-44 | A[1] | CN | H | $NPh_2$ |
| D-45 | A[1] | H | CN | $NPh_2$ |
| D-46 | B[1] | H | H | H |
| D-47 | B[1] | H | H | $OCH_3$ |
| D-48 | B[1] | H | H | $OCH_2CH_3$ |
| D-49 | B[1] | H | H | O-n-butyl |
| D-50 | B[1] | H | H | O-iso-butyl |
| D-51 | B[1] | H | H | O-2-butyl |
| D-52 | B[1] | H | H | O-2-ethylhexyl |
| D-53 | B[1] | H | H | $N(CH_3)_2$ |
| D-54 | B[1] | H | H | $NPh_2$ |
| D-55 | B[1] | H | $CF_3$ | H |
| D-56 | B[1] | $CF_3$ | H | H |
| D-57 | B[1] | H | $CF_3$ | $OCH_3$ |
| D-58 | B[1] | $CF_3$ | H | $OCH_3$ |
| D-59 | B[1] | H | $CF_3$ | $OCH_2CH_3$ |
| D-60 | B[1] | $CF_3$ | H | $OCH_2CH_3$ |
| D-61 | B[1] | H | $CF_3$ | O-n-butyl |
| D-62 | B[1] | $CF_3$ | H | O-n-butyl |
| D-63 | B[1] | H | $CF_3$ | O-iso-butyl |
| D-64 | B[1] | $CF_3$ | H | O-iso-butyl |
| D-65 | B[1] | H | $CF_3$ | O-2-butyl |
| D-66 | B[1] | $CF_3$ | H | O-2-butyl |
| D-67 | B[1] | H | $CF_3$ | O-2-ethylhexyl |
| D-68 | B[1] | $CF_3$ | H | O-2-ethylhexyl |
| D-69 | B[1] | H | $CF_3$ | $N(CH_3)_2$ |
| D-70 | B[1] | $CF_3$ | H | $N(CH_3)_2$ |
| D-71 | B[1] | H | $CF_3$ | $NPh_2$ |
| D-72 | B[1] | $CF_3$ | H | $NPh_2$ |
| D-73 | B[1] | H | CN | H |
| D-74 | B[1] | CN | H | H |
| D-75 | B[1] | CN | H | $OCH_3$ |
| D-76 | B[1] | H | CN | $OCH_3$ |
| D-77 | B[1] | CN | H | $OCH_2CH_3$ |
| D-78 | B[1] | H | CN | $OCH_2CH_3$ |
| D-79 | B[1] | CN | H | O-n-butyl |
| D-80 | B[1] | H | CN | O-n-butyl |
| D-81 | B[1] | CN | H | O-iso-butyl |
| D-82 | B[1] | H | CN | O-iso-butyl |
| D-83 | B[1] | CN | H | O-2-butyl |
| D-84 | B[1] | H | CN | O-2-butyl |
| D-85 | B[1] | CN | H | O-2-ethylhexyl |
| D-86 | B[1] | H | CN | O-2-ethylhexyl |
| D-87 | B[1] | CN | H | $N(CH_3)_2$ |
| D-88 | B[1] | H | CN | $N(CH_3)_2$ |
| D-89 | B[1] | CN | H | $NPh_2$ |
| D-99 | B[1] | H | CN | $NPh_2$ |
| D-100 | C[1] | H | H | H |
| D-101 | C[1] | H | H | $OCH_3$ |
| D-102 | C[1] | H | H | $OCH_2CH_3$ |
| D-103 | C[1] | H | H | O-n-butyl |
| D-104 | C[1] | H | H | O-iso-butyl |
| D-105 | C[1] | H | H | O-2-butyl |
| D-106 | C[1] | H | H | O-2-ethylhexyl |
| D-107 | C[1] | H | H | $N(CH_3)_2$ |
| D-108 | C[1] | H | H | $NPh_2$ |
| D-109 | C[1] | H | $CF_3$ | H |
| D-110 | C[1] | $CF_3$ | H | H |
| D-111 | C[1] | H | $CF_3$ | $OCH_3$ |
| D-112 | C[1] | $CF_3$ | H | $OCH_3$ |
| D-113 | C[1] | H | $CF_3$ | $OCH_2CH_3$ |
| D-114 | C[1] | $CF_3$ | H | $OCH_2CH_3$ |
| D-115 | C[1] | H | $CF_3$ | O-n-butyl |
| D-116 | C[1] | $CF_3$ | H | O-n-butyl |
| D-117 | C[1] | H | $CF_3$ | O-iso-butyl |
| D-118 | C[1] | $CF_3$ | H | O-iso-butyl |
| D-119 | C[1] | H | $CF_3$ | O-2-butyl |
| D-120 | C[1] | $CF_3$ | H | O-2-butyl |
| D-121 | C[1] | H | $CF_3$ | O-2-ethylhexyl |
| D-122 | C[1] | $CF_3$ | H | O-2-ethylhexyl |
| D-123 | C[1] | H | $CF_3$ | $N(CH_3)_2$ |
| D-124 | C[1] | $CF_3$ | H | $N(CH_3)_2$ |
| D-125 | C[1] | H | $CF_3$ | $NPh_2$ |
| D-126 | C[1] | $CF_3$ | H | $NPh_2$ |
| D-127 | C[1] | H | CN | H |
| D-128 | C[1] | CN | H | H |
| D-129 | C[1] | CN | H | $OCH_3$ |
| D-130 | C[1] | H | CN | $OCH_3$ |
| D-131 | C[1] | CN | H | $OCH_2CH_3$ |
| D-132 | C[1] | H | CN | $OCH_2CH_3$ |
| D-133 | C[1] | CN | H | O-n-butyl |
| D-134 | C[1] | H | CN | O-n-butyl |
| D-135 | C[1] | CN | H | O-iso-butyl |
| D-136 | C[1] | H | CN | O-iso-butyl |
| D-137 | C[1] | CN | H | O-2-butyl |
| D-138 | C[1] | H | CN | O-2-butyl |
| D-139 | C[1] | CN | H | O-2-ethylhexyl |
| D-140 | C[1] | H | CN | O-2-ethylhexyl |
| D-141 | C[1] | CN | H | $N(CH_3)_2$ |
| D-142 | C[1] | H | CN | $N(CH_3)_2$ |
| D-143 | C[1] | H | CN | $NPh_2$ |
| D-144 | C[1] | CN | H | $NPh_2$ |
| D-145 | D[1] | H | H | H |
| D-146 | D[1] | H | H | $OCH_3$ |
| D-147 | D[1] | H | H | $OCH_2CH_3$ |
| D-148 | D[1] | H | H | O-n-butyl |
| D-149 | D[1] | H | H | O-iso-butyl |
| D-150 | D[1] | H | H | O-2-butyl |
| D-151 | D[1] | H | H | O-2-ethylhexyl |
| D-152 | D[1] | H | H | $N(CH_3)_2$ |
| D-153 | D[1] | H | H | $NPh_2$ |
| D-154 | D[1] | H | $CF_3$ | H |
| D-155 | D[1] | $CF_3$ | H | H |
| D-156 | D[1] | H | $CF_3$ | $OCH_3$ |
| D-157 | D[1] | $CF_3$ | H | $OCH_3$ |
| D-158 | D[1] | H | $CF_3$ | $OCH_2CH_3$ |
| D-159 | D[1] | $CF_3$ | H | $OCH_2CH_3$ |
| D-160 | D[1] | H | $CF_3$ | O-n-butyl |
| D-161 | D[1] | $CF_3$ | H | O-n-butyl |
| D-162 | D[1] | H | $CF_3$ | O-iso-butyl |
| D-163 | D[1] | $CF_3$ | H | O-iso-butyl |
| D-164 | D[1] | H | $CF_3$ | O-2-butyl |
| D-165 | D[1] | $CF_3$ | H | O-2-butyl |
| D-166 | D[1] | H | $CF_3$ | O-2-ethylhexyl |
| D-167 | D[1] | $CF_3$ | H | O-2-ethylhexyl |
| D-168 | D[1] | H | $CF_3$ | $N(CH_3)_2$ |
| D-169 | D[1] | $CF_3$ | H | $N(CH_3)_2$ |
| D-170 | D[1] | H | $CF_3$ | $NPh_2$ |
| D-171 | D[1] | $CF_3$ | H | $NPh_2$ |
| D-172 | D[1] | H | CN | H |
| D-173 | D[1] | CN | H | H |
| D-174 | D[1] | CN | H | $OCH_3$ |
| D-175 | D[1] | H | CN | $OCH_3$ |
| D-176 | D[1] | CN | H | $OCH_2CH_3$ |
| D-177 | D[1] | H | CN | $OCH_2CH_3$ |
| D-178 | D[1] | CN | H | O-n-butyl |
| D-179 | D[1] | H | CN | O-n-butyl |
| D-180 | D[1] | CN | H | O-iso-butyl |
| D-181 | D[1] | H | CN | O-iso-butyl |
| D-182 | D[1] | CN | H | O-2-butyl |
| D-183 | D[1] | H | CN | O-2-butyl |
| D-184 | D[1] | CN | H | O-2-ethylhexyl |
| D-185 | D[1] | H | CN | O-2-ethylhexyl |
| D-186 | D[1] | CN | H | $N(CH_3)_2$ |
| D-187 | D[1] | H | CN | $N(CH_3)_2$ |
| D-188 | D[1] | CN | H | $NPh_2$ |
| D-189 | D[1] | H | CN | $NPh_2$ |
| D-190 | F[1] | H | H | H |
| D-191 | F[1] | H | H | $OCH_3$ |
| D-192 | F[1] | H | H | $OCH_2CH_3$ |
| D-193 | F[1] | H | H | O-n-butyl |
| D-194 | F[1] | H | H | O-iso-butyl |
| D-195 | F[1] | H | H | O-2-butyl |
| D-196 | F[1] | H | H | O-2-ethylhexyl |
| D-197 | F[1] | H | H | $N(CH_3)_2$ |
| D-198 | F[1] | H | H | $NPh_2$ |
| D-199 | F[1] | H | $CF_3$ | H |
| D-200 | F[1] | $CF_3$ | H | H |

| | | | | |
|---|---|---|---|---|
| D-201 | F[1] | H | CF₃ | OCH₃ |
| D-202 | F[1] | CF₃ | H | OCH₃ |
| D-203 | F[1] | H | CF₃ | OCH₂CH₃ |
| D-204 | F[1] | CF₃ | H | OCH₂CH₃ |
| D-205 | F[1] | H | CF₃ | O-n-butyl |
| D-206 | F[1] | CF₃ | H | O-n-butyl |
| D-207 | F[1] | H | CF₃ | O-iso-butyl |
| D-208 | F[1] | CF₃ | H | O-iso-butyl |
| D-209 | F[1] | H | CF₃ | O-2-butyl |
| D-210 | F[1] | CF₃ | H | O-2-butyl |
| D-211 | F[1] | H | CF₃ | O-2-ethylhexyl |
| D-212 | F[1] | CF₃ | H | O-2-ethylhexyl |
| D-213 | F[1] | H | CF₃ | N(CH₃)₂ |
| D-214 | F[1] | CF₃ | H | N(CH₃)₂ |
| D-215 | F[1] | H | CF₃ | NPh₂ |
| D-216 | F[1] | CF₃ | H | NPh₂ |
| D-217 | F[1] | H | CN | H |
| D-218 | F[1] | CN | H | H |
| D-219 | F[1] | CN | H | OCH₃ |
| D-220 | F[1] | H | CN | OCH₃ |
| D-221 | F[1] | CN | H | OCH₂CH₃ |
| D-222 | F[1] | H | CN | OCH₂CH₃ |
| D-223 | F[1] | CN | H | O-n-butyl |
| D-224 | F[1] | H | CN | O-n-butyl |
| D-225 | F[1] | CN | H | O-iso-butyl |
| D-226 | F[1] | H | CN | O-iso-butyl |
| D-227 | F[1] | CN | H | O-2-butyl |
| D-228 | F[1] | H | CN | O-2-butyl |
| D-229 | F[1] | CN | H | O-2-ethylhexyl |
| D-230 | F[1] | H | CN | O-2-ethylhexyl |
| D-231 | F[1] | CN | H | N(CH₃)₂ |
| D-232 | F[1] | H | CN | N(CH₃)₂ |
| D-233 | F[1] | CN | H | NPh₂ |
| D-234 | F[1] | H | CN | NPh₂ |
| D-235 | E[1] | H | H | H |
| D-236 | E[1] | H | H | OCH₃ |
| D-237 | E[1] | H | H | OCH₂CH₃ |
| D-238 | E[1] | H | H | O-n-butyl |
| D-239 | E[1] | H | H | O-iso-butyl |
| D-240 | E[1] | H | H | O-2-butyl |
| D-241 | E[1] | H | H | O-2-ethylhexyl |
| D-242 | E[1] | H | H | N(CH₃)₂ |
| D-243 | E[1] | H | H | NPh₂ |
| D-244 | E[1] | H | CF₃ | H |
| D-245 | E[1] | CF₃ | H | H |
| D-246 | E[1] | H | CF₃ | OCH₃ |
| D-247 | E[1] | CF₃ | H | OCH₃ |
| D-248 | E[1] | H | CF₃ | OCH₂CH₃ |
| D-249 | E[1] | CF₃ | H | OCH₂CH₃ |
| D-250 | E[1] | H | CF₃ | O-n-butyl |
| D-251 | E[1] | CF₃ | H | O-n-butyl |
| D-252 | E[1] | H | CF₃ | O-iso-butyl |
| D-253 | E[1] | CF₃ | H | O-iso-butyl |
| D-254 | E[1] | H | CF₃ | O-2-butyl |
| D-255 | E[1] | CF₃ | H | O-2-butyl |
| D-256 | E[1] | H | CF₃ | O-2-ethylhexyl |
| D-257 | E[1] | CF₃ | H | O-2-ethylhexyl |
| D-258 | E[1] | H | CF₃ | N(CH₃)₂ |
| D-259 | E[1] | CF₃ | H | N(CH₃)₂ |
| D-260 | E[1] | H | CF₃ | NPh₂ |
| D-261 | E[1] | CF₃ | H | NPh₂ |
| D-262 | E[1] | H | CN | H |
| D-263 | E[1] | CN | H | H |
| D-264 | E[1] | CN | H | OCH₃ |
| D-265 | E[1] | H | CN | OCH₃ |
| D-266 | E[1] | CN | H | OCH₂CH₃ |
| D-267 | E[1] | H | CN | OCH₂CH₃ |
| D-268 | E[1] | CN | H | O-n-butyl |
| D-269 | E[1] | H | CN | O-n-butyl |
| D-270 | E[1] | CN | H | O-iso-butyl |
| D-271 | E[1] | H | CN | O-iso-butyl |
| D-272 | E[1] | CN | H | O-2-butyl |
| D-273 | E[1] | H | CN | O-2-butyl |
| D-274 | E[1] | CN | H | O-2-ethylhexyl |
| D-275 | E[1] | H | CN | O-2-ethylhexyl |
| D-276 | E[1] | CN | H | N(CH₃)₂ |
| D-277 | E[1] | H | CN | N(CH₃)₂ |
| D-278 | E[1] | CN | H | NPh₂ |
| D-279 | E[1] | H | CN | NPh₂ |

[1]

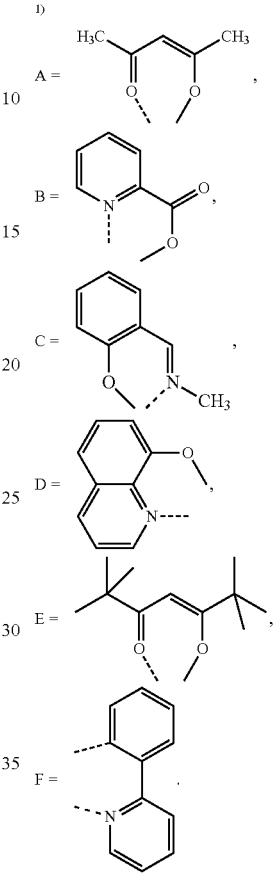

Blocking Layers

In addition to suitable hosts, an OLED device employing a phosphorescent material often requires at least one exciton or hole blocking layers to help confine the excitons or electron-hole recombination centers to the light-emitting layer comprising the host and phosphorescent material, or to reduce the number of charge carriers (electrons or holes). In one embodiment, such a blocking layer would be placed between the electron-transporting layer and the light-emitting layer. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO00/70655 and WO01/93642. Two examples of useful materials are bathocuproine (BCP) and bis(2-methyl-8-quinolinolato)(4-phenylphenolato)aluminum(III) (BAlQ). Metal complexes other than BAlq are also known to block holes and excitons as described in US20030068528. US20030175553 describes the use of fac-tris(1-phenylpyrazolato-N,C 2)iridium(III) (Irppz) in an electron/exciton blocking layer.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

General Device Architecture

The compounds of the present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers. The essential requirements of an OLED are an anode, a cathode, and an organic light-emitting layer located between the anode and cathode. Additional layers may be employed as more fully described hereafter.

A typical structure, especially useful for of a small molecule device, is is comprised of a substrate, an anode, a hole-injecting layer, a hole-transporting layer, a light-emitting layer, a hole- or exciton-blocking layer, an electron-transporting layer, and a cathode. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

Substrate

The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862 and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP1076368, U.S. Pat. Nos. 6,278,236 and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP0732868, laser ablation, and selective chemical vapor deposition.

Hole-Injecting Layer (HIL)

A hole-injecting layer may be provided between anode and hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine). Alternative hole-injecting materials reportedly useful in organic EL devices are described in EP0891121 and EP1029909.

Hole-Transporting Layer (HTL)

The hole-transporting layer of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated in U.S. Pat. No. 3,180,730. Other suitable triarylamines substituted with one or more vinyl radicals and/or comprising at least one active hydrogen containing group are disclosed in U.S. Pat. Nos. 3,567,450 and 3,658,520. A more preferred class of aromatic tertiary amines are those which include at least two aromatic tertiary amine moieties as described in U.S. Pat. Nos. 4,720,432 and 5,061,569. Such compounds include those represented by structural formula

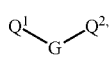
(A)

wherein $Q^1$ and $Q^2$ are independently selected aromatic tertiary amine moieties and G is a linking group such as an arylene, cycloalkylene, or alkylene group of a carbon to carbon bond. In one embodiment, at least one of $Q^1$ or $Q^2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula

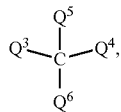
(B)

where $Q^3$ and $Q^4$ each independently represents a hydrogen atom, an aryl group, or an alkyl group or $Q^3$ and $Q^4$ together represent the atoms completing a cycloalkyl group; and $Q^5$ and $Q^6$ each independently represents an aryl group, which is in turn substituted with a diaryl substituted amino group, as indicated by structural formula

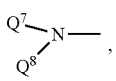
(C)

wherein $Q^7$ and $Q^8$ are independently selected aryl groups. In one embodiment, at least one of $Q^7$ or $Q^8$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula

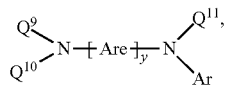
(D)

wherein each Are is an independently selected arylene group, such as a phenylene or anthracene moiety, n is an integer of from 1 to 4, and Ar, $Q^9$, $Q^{10}$, and $Q^{11}$ are independently selected aryl groups. In a typical embodiment, at least one of Ar, $Q^9$, $Q^{10}$, and $Q^{11}$ is a polycyclic fused ring structure, e.g., a naphthalene. The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D).

When a triarylamine is employed in combination with a tetraaryldiamine, the latter is positioned as a layer interposed between the triarylamine and the electron injecting and transporting layer. Illustrative of useful aromatic tertiary amines are the following: 1,1-Bis(4-di-p-tolylaminophenyl) cyclohexane, 1,1-bis(4-di-p-tolylaminophenyl)-4-phenylcyclohexane, N,N,N',N'-tetraphenyl-4,4'''-diamino-1,1':4',1'': 4'', 1'''-quaterphenyl bis(4-dimethylamino-2-methylphenyl) phenylmethane, 1,4-bis[2-[4-[N,N-di(p-toly)amino]phenyl] vinyl]benzene (BDTAPVB), N,N,N',N'-tetra-p-tolyl-4,4'-diaminobiphenyl, N,N,N',N'-tetraphenyl-4,4'-diaminobiphenyl, N,N,N',N'-tetra-1-naphthyl-4,4'-diaminobiphenyl, N,N,N',N'-tetra-2-naphthyl-4,4'-diaminobiphenyl, N-phenylcarbazole, 4,4'-bis[N-(1-naphthyl)-N-phenylamino]biphenyl (NPB), 4,4'-bis[N-(1-naphthyl)-N-(2-naphthyl)amino]biphenyl (TNB), 4,4'-bis [N-(1-naphthyl)-N-phenylamino]p-terphenyl, 4,4'-bis[N-(2-naphthyl)-N-phenylamino]biphenyl, 4,4'-bis[N-(3-acenaphthenyl)-N-phenylamino]biphenyl, 1,5-bis[N-(1-naphthyl)-N-phenylamino]naphthalene, 4,4'-bis[N-(9-anthryl)-N-phenylamino]biphenyl, 4,4'-bis[N-(1-anthryl)-N-phenylamino]-p-terphenyl, 4,4'-bis[N-(2-phenanthryl)-N-phenylamino]biphenyl, 4,4'-bis[N-(8-fluoranthenyl)-N-phenylamino]biphenyl, 4,4'-bis[N-(2-pyrenyl)-N-phenylamino]biphenyl, 4,4'-bis[N-(2-naphthacenyl)-N-phenylamino]biphenyl, 4,4'-bis[N-(2-perylenyl)-N-phenylamino]biphenyl, 4,4'-bis[N-(1-coronenyl)-N-phenylamino]biphenyl, 2,6-bis(di-p-tolylamino) naphthalene, 2,6-bis[di-(1-naphthyl)amino]naphthalene, 2,6-bis[N-(1-naphthyl)-N-(2-naphthyl)amino]naphthalene, N,N,N',N'-tetra(2-naphthyl)-4,4''-diamino-p-terphenyl, 4,4'-bis {N-phenyl-N-[4-(1-naphthyl)-phenyl]amino}biphenyl, 2,6-bis[N,N-di(2-naphthyl)amino]fluorine, 4,4',4''-tris[(3-methylphenyl)phenylamino]triphenylamine (MTDATA), and 4,4'-Bis[N-(3-methylphenyl)-N-phenylamino]biphenyl (TPD). A hole transport layer may be used to enhance conductivity. NPD and TPD are examples of intrinsic hole transport layers. An example of a p-doped hole transport layer is m-MTDATA doped with $F_4$-TCNQ at a molar ratio of 50:1 as disclosed in U.S. Pat. No. 6,337,102 or DE10058578.

Another class of useful hole-transporting materials includes polycyclic aromatic compounds as described in EP1009041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Fluorescent Light-Emitting Materials and Layers (LEL)

In addition to the phosphorescent materials, other light emitting materials may be used in the OLED device, including fluorescent materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials. One skilled in the art will understand that triplet excited state energies of materials in the same layer as the phosphorescent material or in an adjacent layer must be appropriately set so as to prevent unwanted quenching. As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material. The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

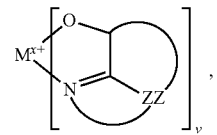

wherein M represents a metal; v is an integer of from 1 to 4; and ZZ independently in each occurrence represents the atoms completing a nucleus having at least two fused aromatic rings. From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed. ZZ completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]

CO-2: Magnesium bisoxine [alias, bis(8-quinolinolato)magnesium(II)]

CO-3: Bis[benzo{f}-8-quinolinolato]zinc(II)

CO-4: Bis(2-methyl-8-quinolinolato)aluminum(III)-μ-oxo-bis(2-methyl-8-quinol-inolato)aluminum(III)

CO-5: Indium trisoxine [alias, tris(8-quinolinolato)indium]

CO-6: Aluminum tris(5-methyloxine) [alias, tris(5-methyl-8-quinolinolato) aluminum(III)]

CO-7: Lithium oxine [alias, (8-quinolinolato)lithium(I)]

CO-8: Gallium oxine [alias, tris(8-quinolinolato)gallium (III)]

CO-9: Zirconium oxine [alias, tetra(8-quinolinolato)zirconium(IV)]

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, compounds L1 to L52 described in U.S. Pat. No. 7,090,930B2.

Electron-Transporting Layer (ETL)

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described. Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Doping may be used to enhance conductivity. Alq3 is an example of an intrinsic electron transport layer. An example of an n-doped electron transport layer is BPhen doped with Li at a molar ratio of 1:1, as disclosed in U.S. Pat. No. 6,337,102.

Deposition of Organic Layers

The organic materials mentioned above are suitably deposited by any means suitable for the form of the organic materials. In the case of small molecules, they are conveniently deposited through thermal evaporation, but can be deposited by other means such as from a solvent with an optional binder to improve film formation. If the material is soluble or in oligomeric/polymeric form, solution processing is usually preferred e.g. spin-coating, ink-jet printing. Dendrimer substituents may be used to enhance the ability of small molecules to undergo solution processing. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiO$_x$, Teflon, and alternating inorganic/polymeric layers are known in the art for encapsulation.

Devices fabricated in accordance with embodiments of the invention may be incorporated into a wide variety of consumer products, including flat panel displays, computer monitors, televisions, billboards, lights for interior or exterior illumination and/or signalling, fully transparent displays, flexible displays, laser printers, cell phones, personal digital assistants (PDAs), laptop computers, digital cameras, camcorders, viewfinders, micro-displays, vehicles, theatre or stadium screen, or a sign. Various control mechanism may be used to control devices fabricated in accordance with the present invention, including passive matrix and active matrix.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

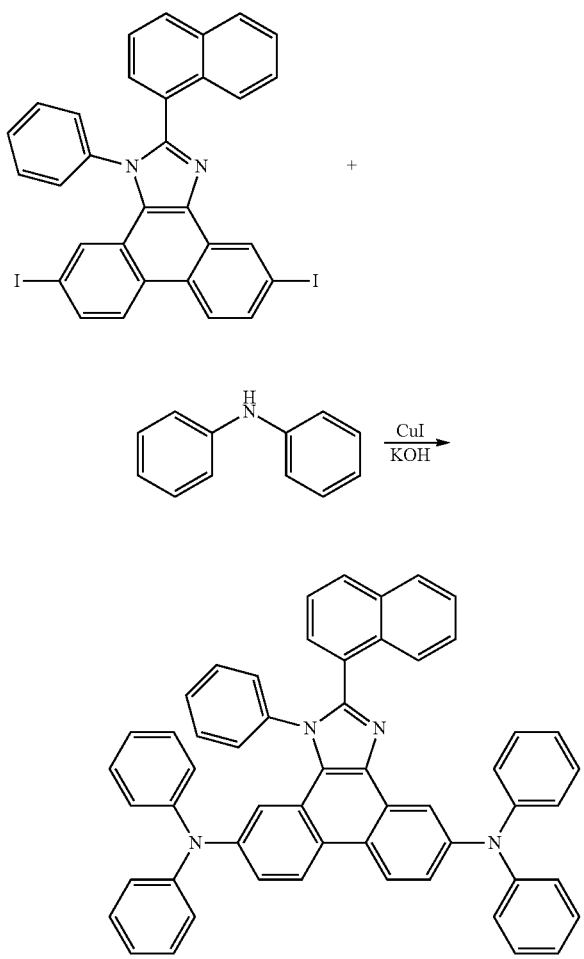

0.80 g of the starting iodide, 0.44 g of diphenylamine, 0.01 g of copper iodide, 0.02 g of 1,10-phenanthroline and 0.53 g of sodium hydroxide are added in this order to 10 ml of dry toluene under an atmosphere of argon. The reaction mixture is heated at 125° C. for one night. The precipitated product is filtered and re-crystallized in 20 ml DMF. 0.40 g of 90% pure product are obtained. The product is purified by column chromatography on silica gel with toluene.

Example 2

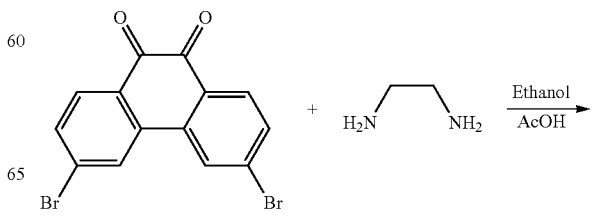

-continued

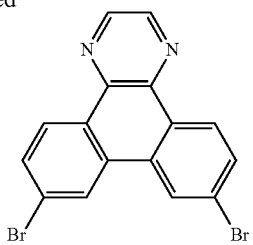

2a) To 12.0 g (32.8 mmol) 3,6-dibromo-phenanthrene-9,10-dione in 300 ml water free ethanol 2.36 g (39.3 mmol) ethanol diamine are added. The reaction mixture is refluxed under nitrogen for 8 h. 500 ml glacial acetic acid are added and the reaction mixture is refluxed for additional 9 h under air and cooled to 25° C. The product is filtered off and washed with ethanol (melting point: 278.0-282.0° C.).

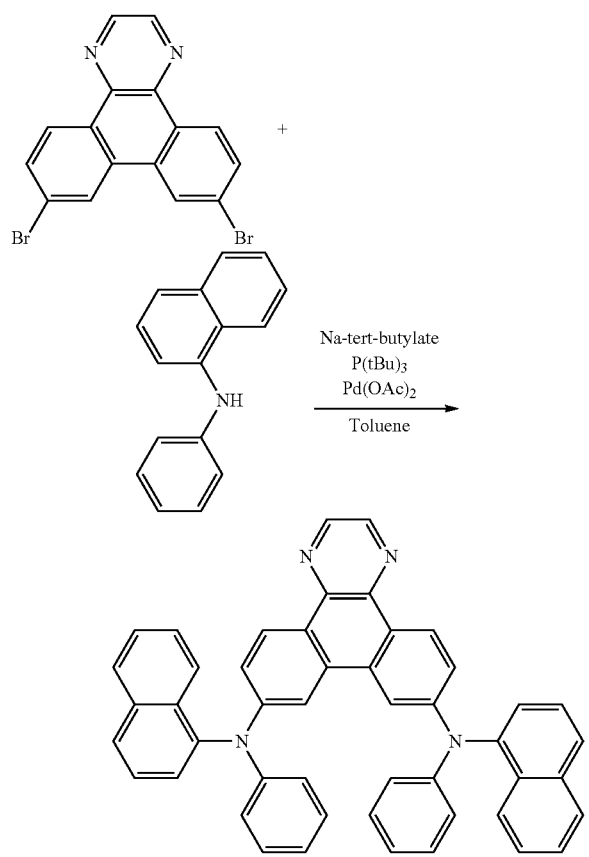

2b) To 3.00 g (7.73 mmol) of the product of example 2a in 60 ml toluene 1.60 g (16.6 mmol) sodium tert-butylate are added. The reaction mixture is degassed with argon. 87 mg (0.39 mmol) palladium (II) acetate are added. The reaction mixture is degassed with argon. 156 mg (0.77 mmol) tri-tert-butylphosphine are added. A degassed solution of 5.26 g (24.0 mmol) N-phenyl-1-naphthylamine in 15 ml toluene is added. The reaction mixture is stirred for 19 h at 90° C. under argon. The reaction mixture is filtered on silica gel with toluene. The solvent is removed in vacuum and the product is crystallized from diethyl ether (melting point: 228-230° C.).

Example 3

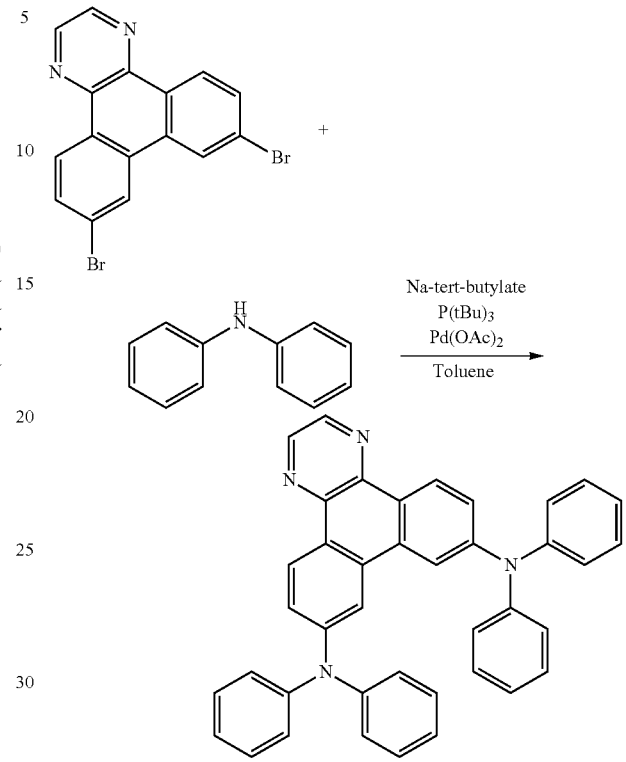

The reaction is carried out according to example 2b except that 4.36 g (11.2 mmol) of the product of example 2b and N-diphenyl amine are used (melting point: 206° C.).

Example 4

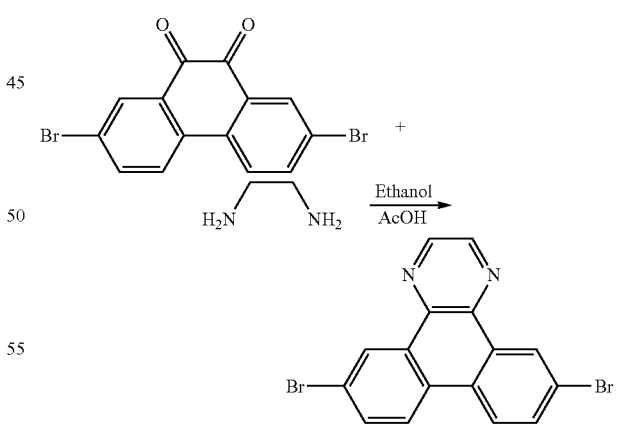

4a) To 20.0 g (54.6 mmol) 2,7-dibromo-phenanthrene-9,10-dione in 300 ml water free ethanol 3.94 g (65.6 mmol) ethanoldiamine are added. The reaction mixture is refluxed under nitrogen for 4 h. 500 ml glacial acetic acid are added and the reaction mixture is refluxed for additional 30 h under air and is cooled to 25° C. The product is filtered off, washed with water and decocted in glacial acetic acid and 2 times in methyl ethyl ketone (melting point: 176.0-179.0° C.)

Example 6

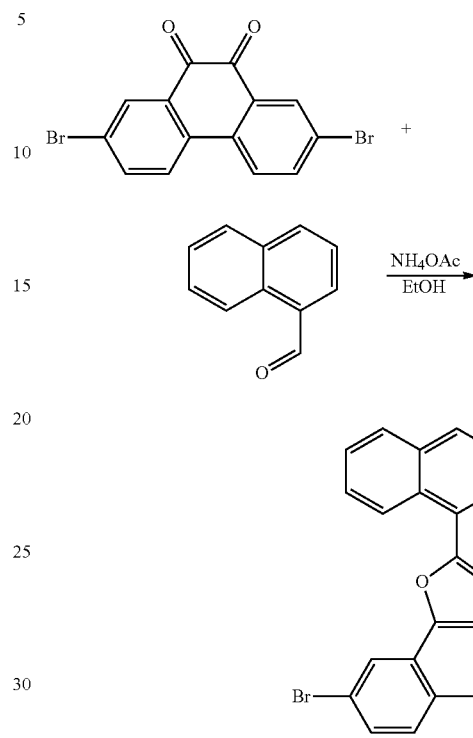

6a) A mixture of 5.0 g (13.7 mmol) 2,7-dibromo-phenanthrene-9,10-dione, 2.56 g (16.4 mmol) 1-naphthalene carboxaldehyde and 5.26 g (68.3 mmol) ammonium acetate in 100 ml ethanol is refluxed under nitrogen for 3 h. The product is filtered off, washed with ethanol, water and ethanol and crystallized from toluene.

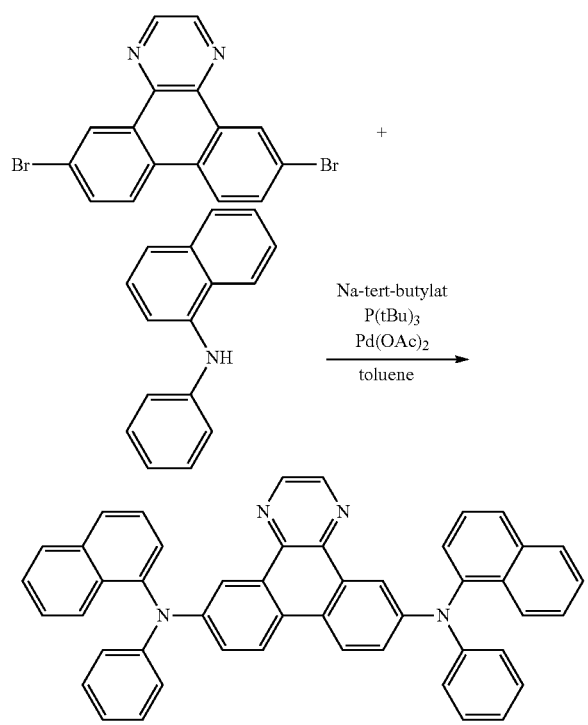

4b) The synthesis is carried out in analogy to example 2b. The product has a melting point of 177° C.

Example 5

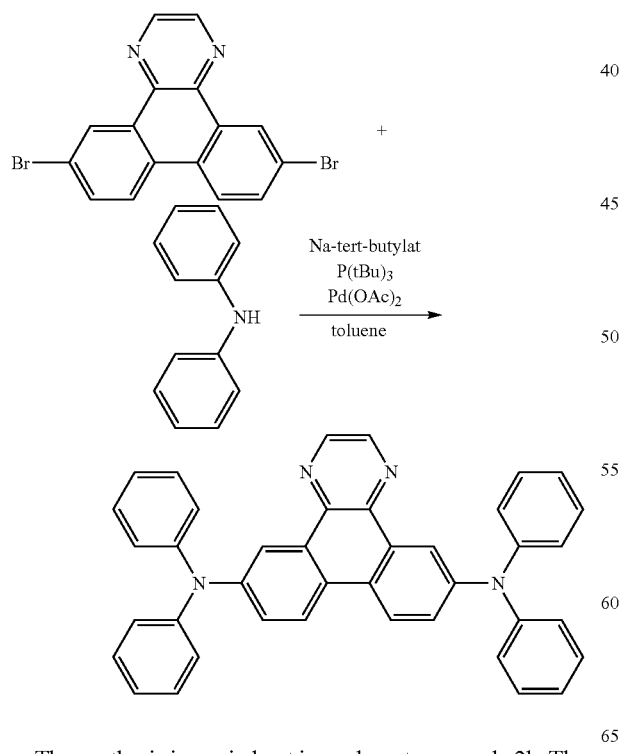

The synthesis is carried out in analogy to example 2b. The product has a melting point of 266.0-267.0° C.

-continued

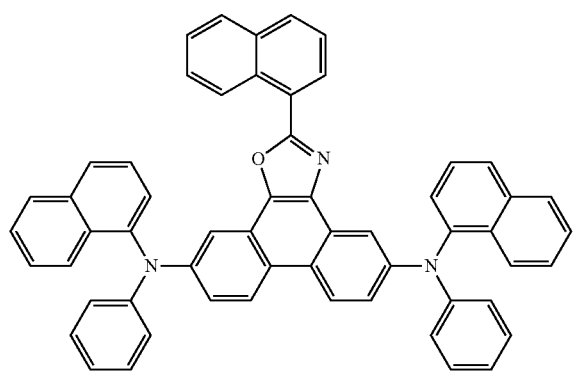

6b) The synthesis is carried out in analogy to example 2b (melting point: 283.0-286.0° C.).

Example 7

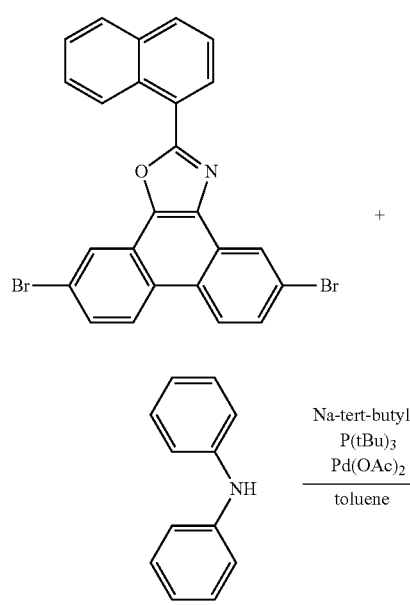

7b) The synthesis is carried out in analogy to example 2b (decomposition point: 380° C.).

Example 8

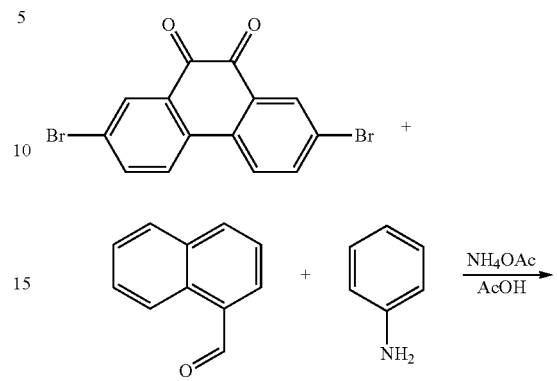

8a) 30.0 g (82.0 mmol) 2,7-dibromo-phenanthrene-9,10-dione, 14.1 g (90.2 mmol) 1-naphthalene carboxaldehyde, 15.3 g (164 mmol) aniline and 19.0 g (246 mmol) ammonium acetate in 500 ml glacial acetic acid are refluxed for 4 h under nitrogen. The product is filtered off, washed with glacial acetic acid, water, a sodium hydrogen carbonate solution and water and then decocted in toluene and methyl ethyl ketone.

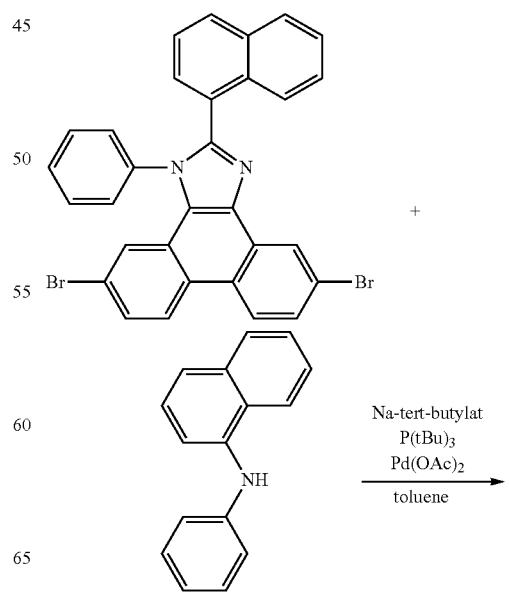

-continued

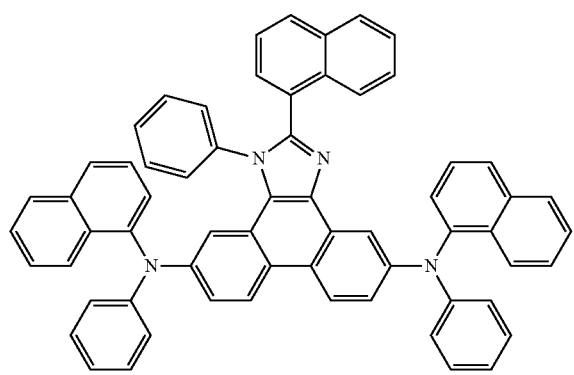

8b) The reaction is carried out according to example 2b. The product has a glass transition point of 158° C.

Example 9

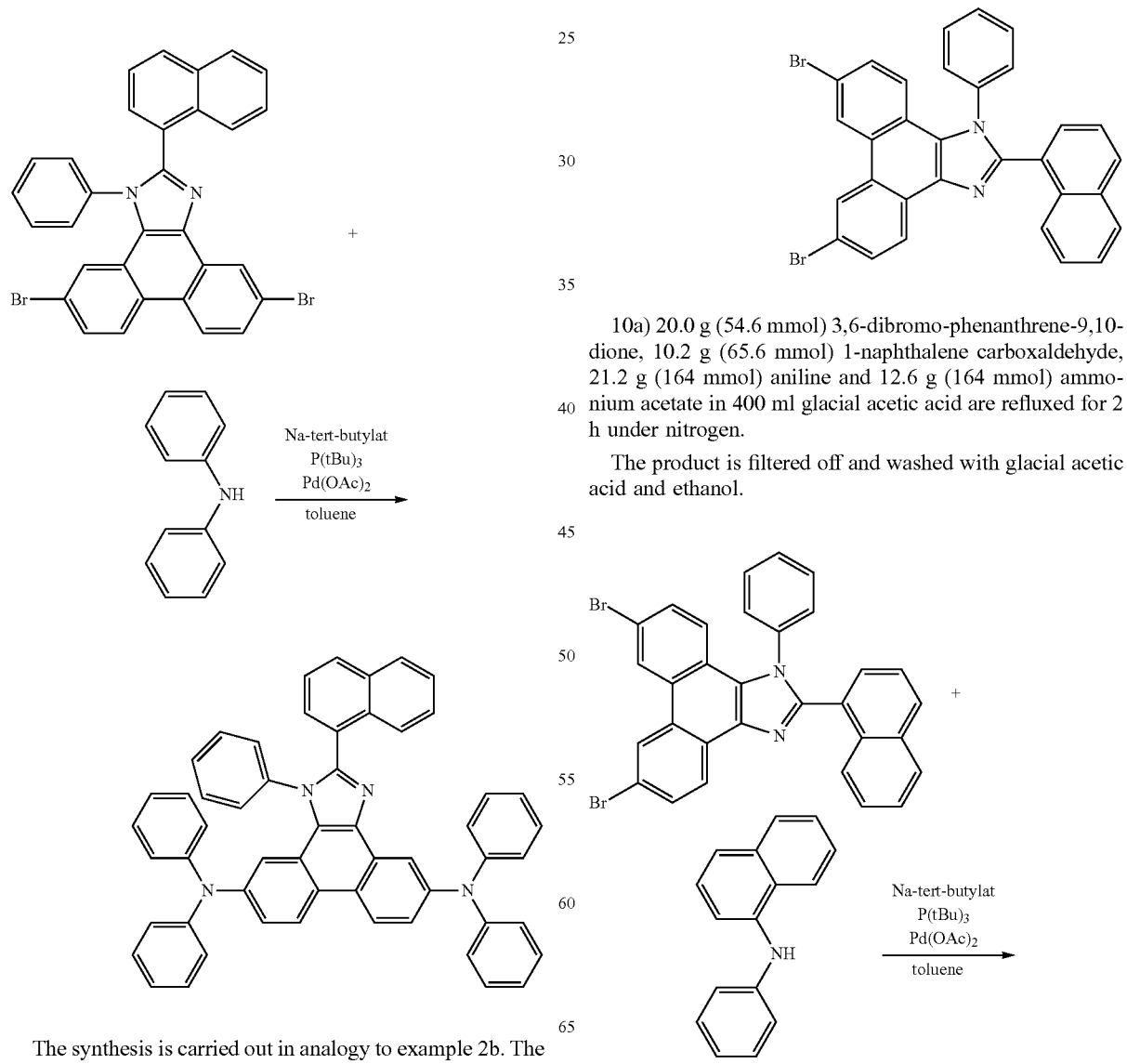

The synthesis is carried out in analogy to example 2b. The product has a melting point of 334° C.

Example 10

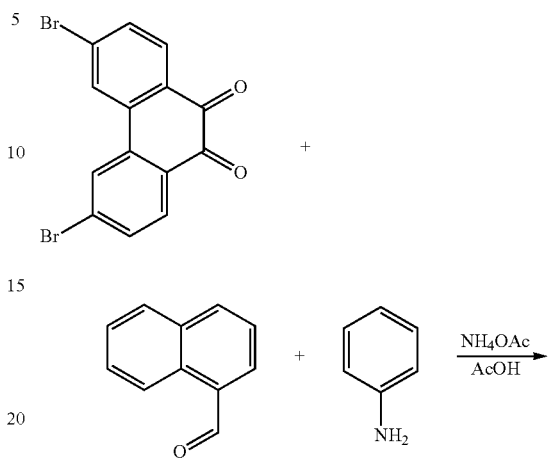

10a) 20.0 g (54.6 mmol) 3,6-dibromo-phenanthrene-9,10-dione, 10.2 g (65.6 mmol) 1-naphthalene carboxaldehyde, 21.2 g (164 mmol) aniline and 12.6 g (164 mmol) ammonium acetate in 400 ml glacial acetic acid are refluxed for 2 h under nitrogen.

The product is filtered off and washed with glacial acetic acid and ethanol.

-continued

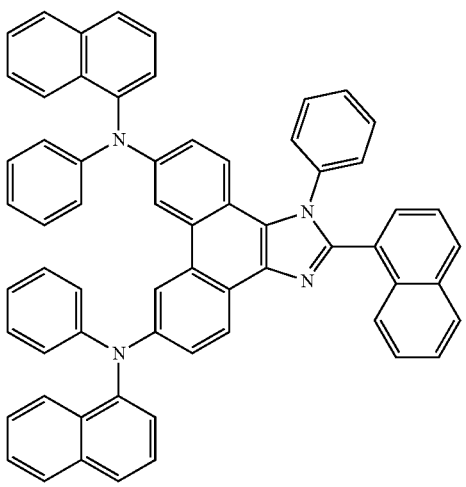

10b) The synthesis is carried out in analogy to example 2b. The product has a melting point of 193.0-195.0° C. ° C. (glass transition point 153° C.).

Example 11

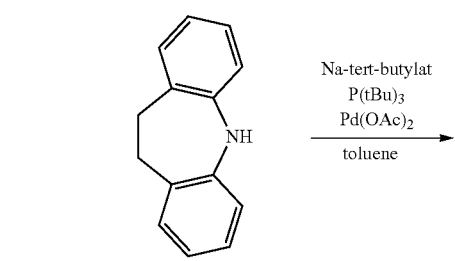

+

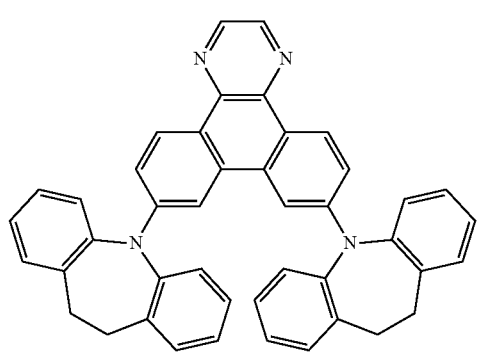

The synthesis is carried out in analogy to example 2b. The product has a melting point of 350° C.

Example 12

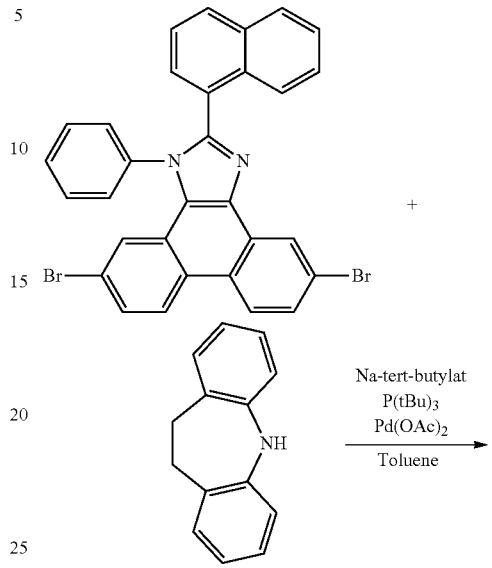

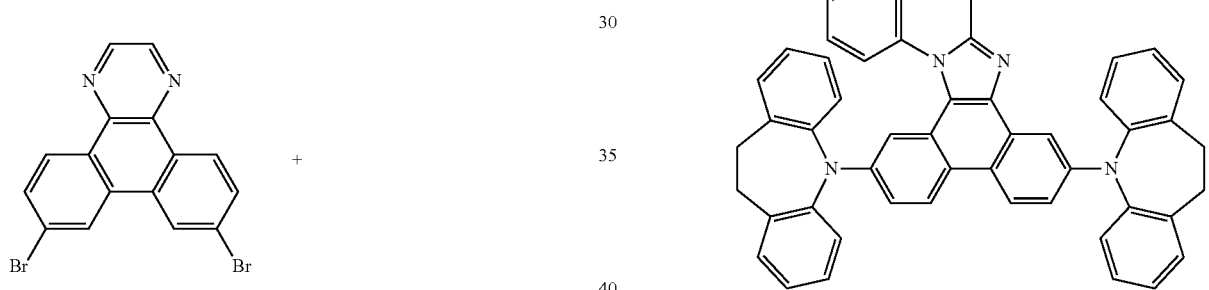

The synthesis is carried out in analogy to example 2b. The product has a melting point of 290° C.

Application Example 1

Device fabrication: Prior to device fabrication, indium tin oxide (ITO) on glass is patterned as 2 mm wide stripes (sheet resistance 20 Ω/square). The substrates were cleaned by sonication in acetone, isopropanol and water for 15 minutes in each solvent. After that, the substrates are dried with a nitrogen steam and treated by $O_2$ vacuum plasma for 5 minutes. Organic layers of the OLEDS are sequentially deposited by thermal evaporation from resistively heated ceramic crucibles at a base pressure of $2\times10^{-7}$ Torr, at 2 A/s. Host and dopant were co-evaporated from different sources to form a thin film of 20 nm thickness.

The evaporation rate of each single component source was controlled by a thickness monitor (Inficon) close to the substrate or to the source. All the devices were measured in a nitrogen glove box, immediately after fabrication.

Current-voltage and optical measurements were carried out with a Botest equipment. Electroluminescent spectra were measured with an Ocean Optic spectrometer.

An OLED is prepared having the following structure from the anode to the cathode: 60 nm of a hole injection layer, such as NHT-5 of Novaled AG, using 10 nm of an improved hole transport layer, such as NHT5:NDP2 of Novaled AG, 20 nm of 4,4'-bis[N-1-naphthyl)-N-phenylamino]-biphenyl (α-NPD), 20 nm of aluminum (III) bis (2-methyl-8-quinolato) 4-phenyl-phenolate (BAlq) doped with 15 wt % of compound obtained in Example 3c/10 nm of BAlq acting as hole blocking layer, 60 nm of an improved electron transport layer, such as NET-5:NDN-1 from Novaled, and 100 nm of aluminium as top electrode.

| EML 15 wt % dopant | Current efficiency [cd/A] @ 1000 cd/m² | Power efficiency [lm/W] @ 1000 Cd/m² | Voltage [V] @ 1000 Cd/m² | CIE X | CIE Y |
|---|---|---|---|---|---|
| Application Example 1 | Host example 8b[1] | 5.5 | 5.3 | 3.3 | 0.68 | 0.32 |
| Application Example 2 | Mixed Host ex. 8b:BAlq 75:10[1] | 5.8 | 5.5 | 3.4 | 0.68 | 0.32 |
| Application Example 3 | Host ex. 10b[1] | 4.8 | 4.1 | 3.7 | 0.68 | 0.32 |
| Application Example 4 | Host ex. 10b[1] | 4.2 | 4.0 | 3.3 | 0.68 | 0.32 |
| Application Example 5 | Host ex. 8b[1] | 6.8 | 6.2 | 3.4 | 0.68 | 0.32 |
| Application Example 6 | Host ex. 5[2] | 6.2 | 5.4 | 3.6 | 0.68 | 0.32 |
| Application Example 7 | Host ex. 3[2] | 6.1 | 6.5 | 2.90 | 0.65 | 0.35 |
| Application Example 8 | Mixed host Ex 3:BAlq 50:50[2] | 8.3 | 8.7 | 3.0 | 0.65 | 0.35 |
| Application Example 9 | Host ex. 8b[2] | 7.9 | 8.8 | 2.82 | 0.65 | 0.35 |
| Application Example 10 | Mixed host Ex. 8b:BAlq 50:50[2] | 9.5 | 9.9 | 2.99 | 0.65 | 0.35 |

[1]using phosphorescent compound obtained in example 4b of European patent application 07102949.0 as dopant in the emissive layer (EML):

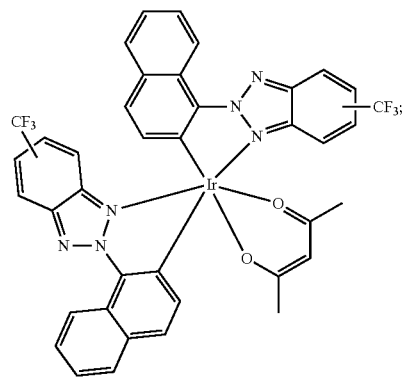

| EML 15 wt % dopant | Current efficiency [cd/A] @ 1000 cd/m² | Power efficiency [lm/W] @ 1000 Cd/m² | Voltage [V] @ 1000 Cd/m² | CIE X | CIE Y |
|---|---|---|---|---|---|

[2]using phosphorescent compound obtained in example 1b of European patent application 07102949.0 as dopant in the emissive layer (EML):

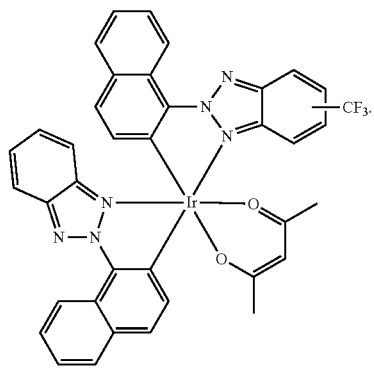

The invention claimed is:

1. An electroluminescent (EL) device, comprising a compound of the formula

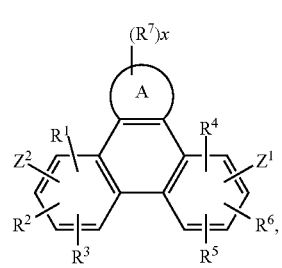

(I)

wherein A is a 6-membered heteroaromatic ring, containing at least one heteroatom selected from nitrogen, oxygen, and sulfur, $Z^1$ is

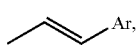

—$NA^1A^1$, —$P(=O)A^4A^{4'}$, or —$SiA^6A^7A^8$ $Z^2$

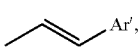

$NA^2A^{2'}$, —$P(=O)A^5A^{6'}$, or —$SiA^{6'}A^{7'}A^{8'}$,

Ar and Ar' are independently of each other $C_6$-$C_{14}$ aryl, which may optionally be substituted by one or more groups selected from $C_1$-$C_{25}$ alkyl which may be optionally interrupted by —O—, or $C_1$-$C_{25}$ alkoxy, $R^1$, $R^2$, $R^3$, $R^4$, $R^5$, and $R^6$ are independently of each other hydrogen, halogen, or an organic substituent, or $R^1$ and $R^2$, $R^4$ and $R^6$, $R^2$ and $R^3$, $R^5$ and $R^3$, and/or $R^5$ and $R^6$, which are adjacent to each other, together form an aromatic or heteroaromatic ring or a ring system which can optionally be substituted, R⁷ is an organic substituent, wherein two or more substituents R⁷ in the same molecule may have different meanings, or can form together an aromatic or heteroaromatic ring or ring system, and x is 0, or an integer of 1 to 5;

$A^1$, $A^2$, $A^{1'}$, and $A^{2'}$ are independently of each other a $C_6$-$C_{24}$ aryl group, a $C_2$-$C_{30}$ heteroaryl group, which can optionally be substituted, or a group

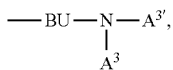

wherein BU is a bridging unit, $A^3$ and $A^{3'}$ are independently or each other a $C_6$-$C_{24}$ aryl group or a $C_2$-$C_{30}$ heteroaryl group, which can optionally be subsituted, or $A^1$ and $A^{1'}$ or $A^2$ and $A^{2'}$ or $A^3$ and $A^{3'}$ together with the nitrogen atom to which they are bonded form a heteroaromatic ring or ring system, $A^4$, $A^{4'}$, $A^6$, $A^7$, $A^8$, $A^5$, $A^{5'}$, $A^{6'}$, $A^{7'}$, and $A^{8'}$ are independently of each other a $C_6$-$C_{24}$ aryl group or a $C_2$-$C_{30}$ heteroaryl group, which can optionally be substituted.

2. The EL device according to claim 1, comprising a compound of formula

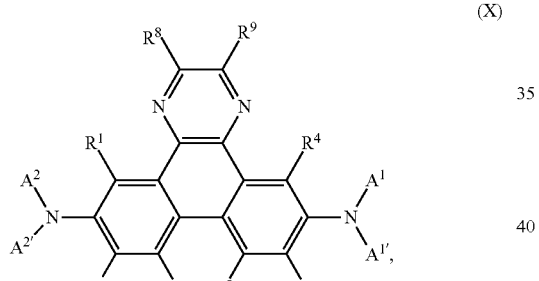

(X)

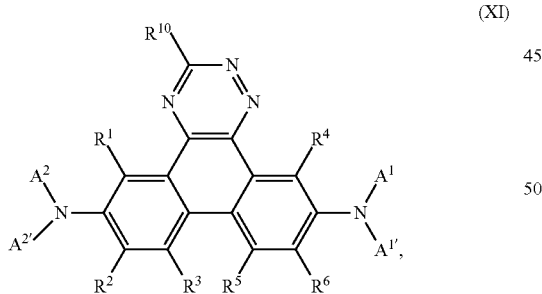

(XI)

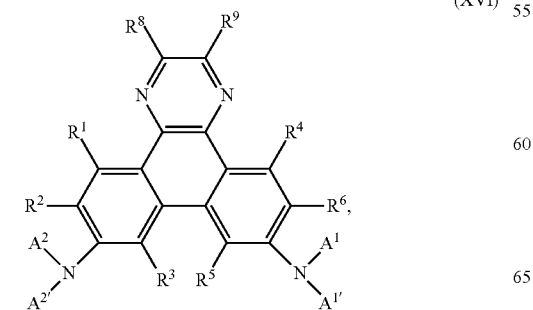

(XVI)

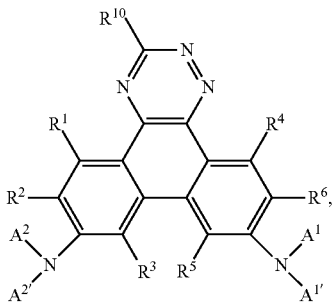

(XVII)

wherein $R^1$ and $R^4$ are independently of each other hydrogen, halogen, $C_1$-$C_{18}$ alkyl, $C_1$-$C_{18}$ alkyl which is substituted by E and/or interrupted by D, $C_1$-$C_{18}$ perfluoroalkyl, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, CN, or —CO—$R^{28}$, $R^2$, $R^3$, $R^5$, and $R^6$ are independently of each other hydrogen, halogen, $C_1$-$C_{18}$ alkyl, $C_1$-$C_{18}$ alkyl which is substituted by E and/or interrupted by D, $C_1$-$C_{18}$ perfluoroalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, CN, or —CO—$R^{28}$, $R^8$ and $R^9$ are independently of each other hydrogen, $C_1$-$C_{18}$ alkyl, $C_1$-$C_{18}$ alkyl which is substituted by E and/or interrupted by D, $C_1$-$C_{18}$ perfluoroalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, CN, or —CO—$R^{28}$, or $R^8$ and $R^9$ together form a group

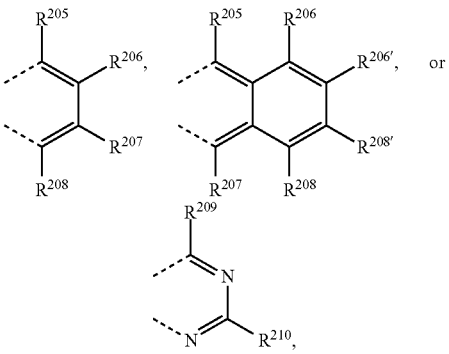

wherein $R^{206'}$, $R^{208'}$, $R^{205}$, $R^{206}$, $R^{207}$, $R^{208}$, $R^{209}$, and $R^{210}$ are independently of each other hydrogen, $C_1$-$C_{18}$ alkyl, $C_1$-$C_{18}$ alkyl which is substituted by E and/or interrupted by D, $C_1$-$C_{18}$ alkoxy, or $C_1$-$C_{18}$ alkoxy which is substituted by E and/or interrupted by D, $C_1$-$C_{18}$ perfluoroalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_7$-$C_{25}$ aralkyl, CN, or —CO—$R^{28}$, $R^{10}$ is hydrogen, $C_1$-$C_{18}$ alkyl, $C_1$-$C_{18}$ alkyl which is substituted by E and/or interrupted by D, $C_1$-$C_{18}$ perfluoroalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, CN, or —CO—$R^{28}$, $R^{8'}$ and $R^{9'}$ are independently of each other hydrogen, CN, CONR$^{25}$R$^{26}$, $C_1$-$C_{18}$ alkyl, $C_1$-$C_{18}$ alkyl which is substituted by E and/or interrupted by D, $C_1$-$C_{18}$ perfluoroalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, or —CO—$R^{28}$, or two substituents $R^1$ and $R^2$, $R^4$ and $R^6$, $R^2$ and $R^3$, and/or $R^5$ and $R^6$, which are adjacent to each other, together form a group

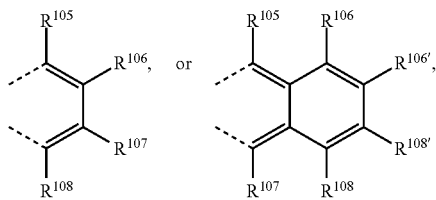

or two substituents $R^5$ and $R^3$, which are adjacent to each other, together form a group

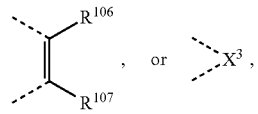

wherein $X^3$ is O, S, C($R^{119}$)($R^{120}$), or NR$^{17}$, $R^{105}$, $R^{106}$, $R^{107}$, $R^{108}$, $R^{106'}$ and $R^{108'}$ are independently hydrogen, $C_1$-$C_{18}$ alkyl, $C_1$-$C_{18}$ alkyl which is substituted by E and/or interrupted by D, $C_1$-$C_{18}$ alkoxy, or $C_1$-$C_{18}$ alkoxy which is substituted by E and/or interrupted by D, $R^{119}$ and $R^{120}$ are independently of each $C_1$-$C_{18}$ alkyl, $C_1$-$C_{18}$ alkyl which is substituted by E and/or interrupted by D, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, or $R^{119}$ and $R^{120}$ together form a group of formula =CR$^{121}$R$^{122}$, wherein $R^{121}$ and $R^{122}$ are independently of each other H, $C_1$-$C_{18}$ alkyl, $C_1$-$C_{18}$ alkyl which is substituted by E and/or interrupted by D, $C_6$-$C_{24}$ aryl, $C_6$-$C_{24}$ aryl which is substituted by G, or $C_2$-$C_{20}$ heteroaryl, or $C_2$-$C_{20}$ heteroaryl which is substituted by G, or $R^{119}$ and $R^{120}$ together form a five or six membered ring, which optionally can be substituted by $C_1$-$C_{18}$ alkyl, $C_1$-$C_{18}$ alkyl which is substituted by E and/or interrupted by D, $C_6$-$C_{24}$ aryl, $C_6$-$C_{14}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, or —C(=O)—$R^2$, and $R^{127}$ is H; $C_6$-$C_{18}$ aryl; $C_6$-$C_{18}$ aryl which is substituted by $C_1$-$C_{18}$ alkyl or $C_1$-$C_{18}$ alkoxy; $C_1$-$C_{18}$ alkyl; or $C_1$-$C_{18}$ alkyl which is interrupted by —O—, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen;

G is E, $C_1$-$C_{18}$ alkyl, $C_1$-$C_{18}$ alkyl which is interrupted by D, $C_1$-$C_{18}$ perfluoroalkyl, $C_1$-$C_{18}$ alkoxy, or $C_1$-$C_{18}$ alkoxy which is substituted by E and/or interrupted by D, wherein $R^{23}$, $R^{24}$, $R^{25}$ and $R^{26}$ are independently of each other H; $C_6$-$C_{18}$ aryl; $C_6$-$C_{18}$ aryl which is substituted by $C_1$-$C_{18}$ alkyl or $C_1$-$C_{18}$ alkoxy; $C_1$-$C_{18}$ alkyl; or $C_1$-$C_{18}$ alkyl which is interrupted by —O—; or $R^{25}$ and $R^{26}$ together form a five or six membered ring, $R^{27}$ and $R^{28}$ are independently of each other H; $C_6$-$C_{18}$ aryl; $C_6$-$C_{18}$ aryl which is substituted by $C_1$-$C_{18}$ alkyl or $C_1$-$C_{18}$ alkoxy; $C_1$-$C_{18}$ alkyl; or $C_1$-$C_{18}$ alkyl which is interrupted by —O—;

$R^{29}$ is H; $C_6$-$C_{18}$ aryl; $C_6$-$C_{18}$ aryl, which is substituted by $C_1$-$C_{18}$ alkyl or $C_1$-$C_{18}$ alkoxy; $C_1$-$C_{18}$ alkyl; or $C_1$-$C_{18}$ alkyl which is interrupted by —O—, $R^{30}$ and $R^{31}$ are independently of each other $C_1$-$C_{18}$ alkyl, $C_6$-$C_{18}$ aryl, or $C_6$-$C_{18}$ aryl which is substituted by $C_1$-$C_{18}$ alkyl, and $R^{32}$ is $C_1$-$C_{18}$ alkyl, $C_6$-$C_{18}$ aryl, or $C_6$-$C_{18}$ aryl which is substituted by $C_1$-$C_{18}$ alkyl.

3. The EL device according to claim 1, comprising a compound of the formula X, or XI, wherein R and $R^4$ are hydrogen, $R^2$, $R^3$, $R^5$ and $R^6$ are independently of each other H, $C_1$-$C_{18}$ alkyl, $C_1$-$C_{18}$ alkyl which is interrupted by D, $C_1$-$C_{18}$ perfluoroalkyl, $C_1$-$C_{18}$ alkoxy, $C_1$-$C_{18}$ alkoxy which is interrupted by D, $C_7$-$C_{25}$ aralkyl, or a group —$X^2$—$R^{18}$, $R^8$ and $R^9$ are independently of each other H, $C_1$-$C_{18}$ alkyl, $C_1$-$C_{18}$ alkyl which is interrupted by D, $C_1$-$C_{18}$ perfluoroalkyl, $C_1$-$C_{18}$ alkoxy, $C_1$-$C_{18}$ alkoxy which is interrupted by D, or a group —$X^2$—$R^{18}$; or two substituents R and $R^3$ and/or $R^5$ and $R^6$, which are adjacent to each other, together form a group

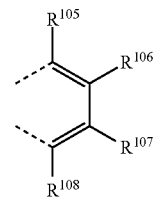

or two substituents $R^5$ and $R^3$, which are adjacent to each other, together form a group

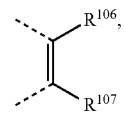

wherein $R^{105}$, $R^{106}$, $R^{107}$ and $R^{108}$ are independently of each other H, or $C_1$-$C_8$alkyl, or $R^8$ and $R^9$ together form a group

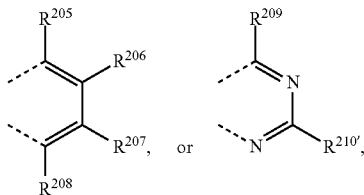

wherein $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$ perfluoroalkyl, $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$ perfluoroalkyl, $C_1$-$C_{18}$alkoxy, $C_1$-$C_{18}$alkoxy which is substituted by E and/or interrupted by D, or a group —$X^2$—$R^{18}$, wherein $X^2$ is a $C_6$-$C_{12}$aryl, or $C_6$-$C_{12}$heteroaryl spacer, which can be substituted one to two times with $C_1$-$C_{18}$alkyl, $C_1$-$C_{18}$alkyl which is interrupted by D, $C_1$-$C_{18}$ perfluoroalkyl, $C_1$-$C_{18}$alkoxy, or $C_1$-$C_{18}$alkoxy which is substituted by E and/or interrupted by D, and $R^8$ is H, $C_1$-$C_{18}$alkyl, $C_1$-$C_{18}$alkyl which is interrupted by D, $C_1$-$C_{18}$ perfluoroalkyl, $C_1$-$C_{18}$alkoxy, $C_1$-$C_{18}$alkoxy which is interrupted by D, or —$NR^{25}R^{26}$;

D is —CO—; —COO—; —S—; —SO—; —$SO_2$—; —O—; —$NR^{25}$—; —$CR^{23}$=$CR^{24}$—; or —C≡C—; wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_8$alkyl or $C_1$-$C_8$alkoxy; $C_1$-$C_8$alkyl; or $C_1$-$C_8$alkyl which is interrupted by —O—, or $R^{25}$ and $R^{26}$ together form a five or six membered ring.

4. The EL device according to claim 1, wherein $A^1$, $A^2$, $A^{1'}$ and $A^{2'}$ are independently of each other

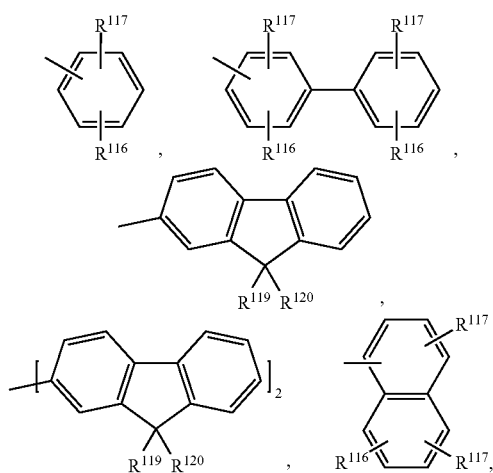

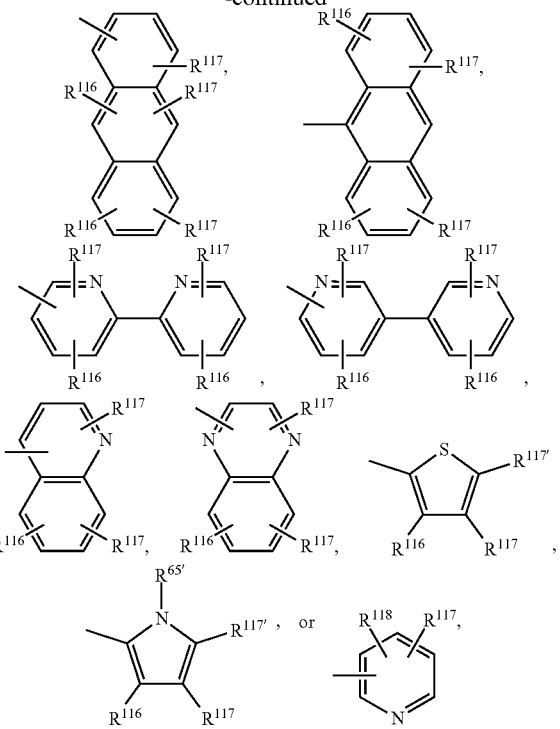

or $A^1$ and $A^{1'}$ or $A^2$ and $A^{2'}$ together with the nitrogen atom to which they are bonded form a heteroaromatic ring system

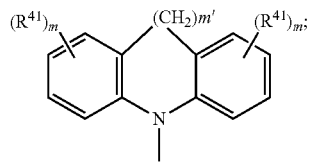

m' is 0, 1, or 2;
m can be the same or different at each occurrence and is 0, 1, 2, or 3;
$R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or
two or more groups $R^{41}$ form a ring system;
$R^{45}$ is H, a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is H, a $C_1$-$C_{25}$alkyl group, or a $C_4$-$C_{18}$cycloalkyl group, $R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{128}$, or substituents $R^{116}$, $R^{117}$ and $R^{117'}$, which are adjacent to each other, can form a ring, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{126}$ and $R^{127}$ are independently of each other H; $C_6$-$C_{18}$aryl; $C_6$-$C_{18}$ aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—, D is —CO—, —COO—, —S—, —SO—, —SO$_2$—, —O—, —N$R^{65}$, —Si$R^{70}R^{71}$—, POR$^{72}$—, —C$R^{63}$=C$R^{64}$—, or —C≡C—, and E is —OR$^{69}$, SR$^{69}$, —N$R^{65}R^{66}$, —COR$^{68}$—COOR$^{67}$, —CONR$^{65}R^{66}$, —CN, or halogen, G is E, or $C_1$-$C_{18}$alkyl, $R^{63}$, $R^{64}$, $R^{65}$, $R^{65}$ and $R^{66}$ are independently of each other H; $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ and $R^{68}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is H; $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl which is substituted by $C_1$-$C_{18}$alkyl, and $R^{72}$ is $C_1$-$C_{18}$alkyl, $C_6$-$C_{18}$aryl, or $C_6$-$C_{18}$aryl which is substituted by $C_1$-$C_{18}$alkyl; or $A^1$, $A^2$, $A^{1'}$ and $A^{2'}$ are independently of each other a group

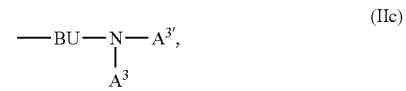
(IIc)

wherein BU is

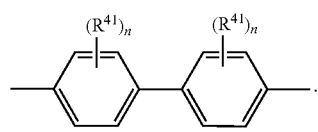

5. The EL device according to claim 1, comprising a compound selected from

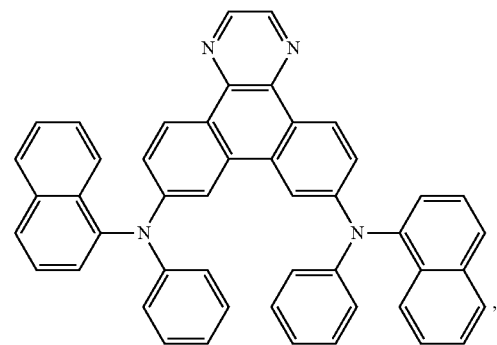

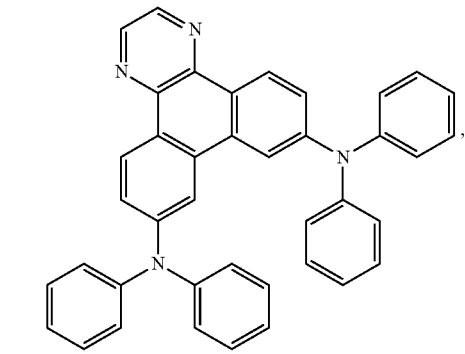

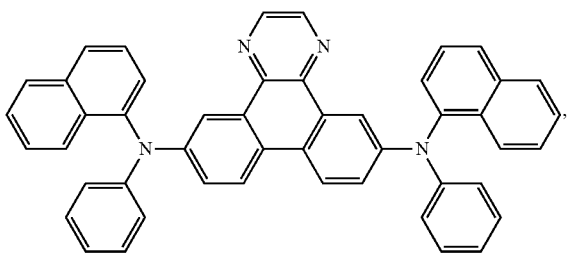

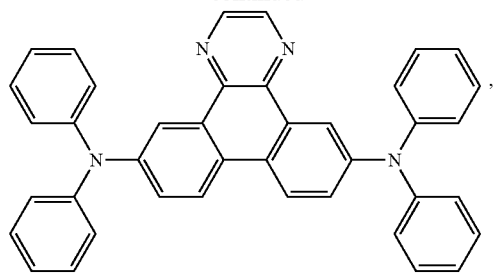

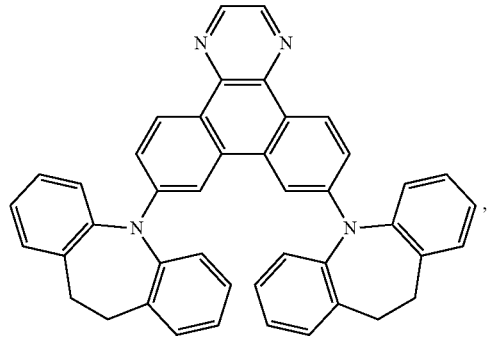

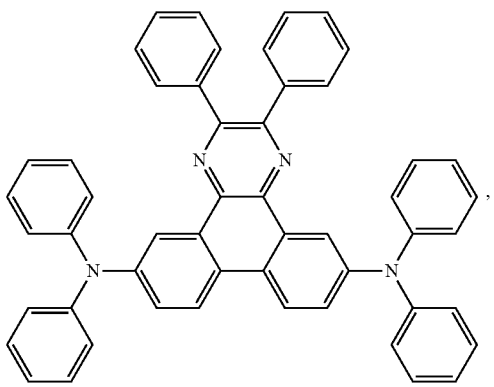

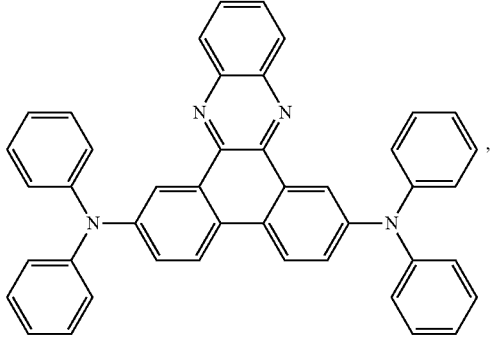

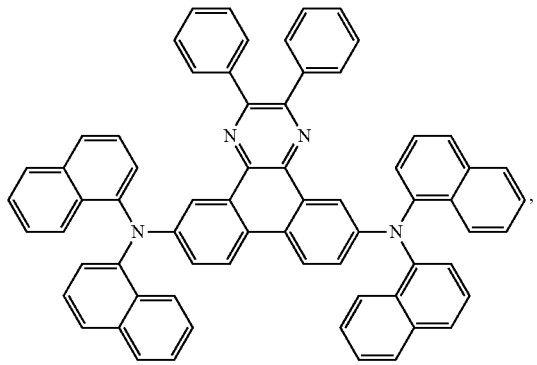

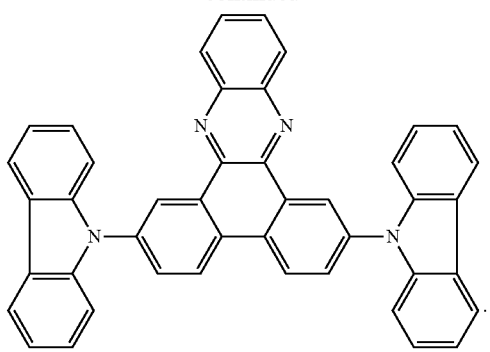

6. Electroluminescent device according to claim 1, comprising a cathode, an anode, and therebetween a light emitting layer containing a host material and a phosphorescent light-emitting material, wherein the host material is a compound of formula I.

7. An electroluminescent (EL) device according to claim 1, comprising a compound of the formula

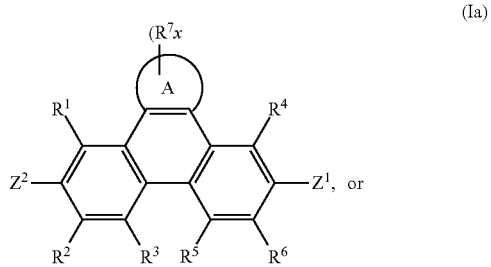

(Ia)

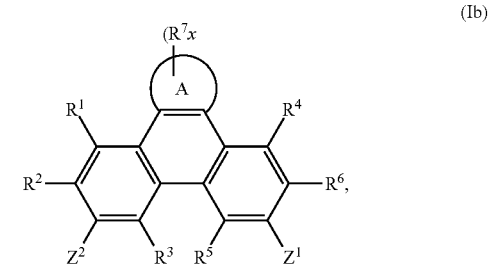

(Ib)

wherein A is a 6-membered heteroaromatic ring, containing one nitrogen atom and at least one further heteroatom selected from nitrogen, substituted nitrogen, oxygen and sulfur, Ar and Ar' are independently of each other phenyl or naphthyl, which may optionally be substituted by one or more groups selected from $C_1$-$C_{25}$alkyl which may optionally be interrupted by —O— or $C_1$-$C_{25}$alkoxy, $A^1$, $A^2$, $A^{1'}$ and $A^{2'}$ are independently of each other a $C_6$-$C_{24}$aryl group, a $C_2$-$C_{30}$heteroaryl group, which can optionally be substituted, or a group

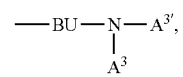

wherein BU is

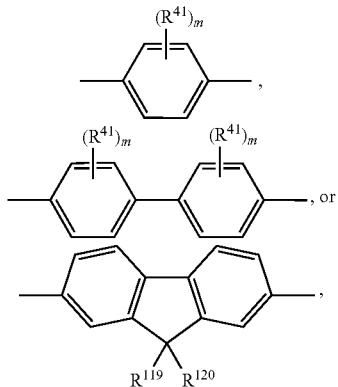

8. A compound of the formula

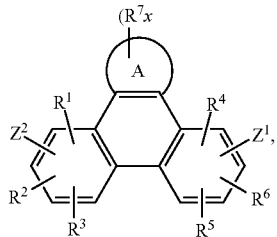
(I)

wherein A is a 6-membered heteroaromatic ring, containing at least one heteroatom selected from nitrogen, oxygen, and sulfur, $Z^1$ is

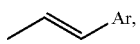

$-NA^1A^{1'}$, $-P(=O)A^4A^{4'}$, or $-SiA^6A^7A^8$ $Z^2$ is

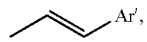

$NA^2A^{2'}$, $-P(=O)A^5A^{6'}$, or $-SiA^{6'}A^{7'}A^{8'}$,

Ar and Ar' are independently of each other $C_6$-$C_{14}$ aryl, which may optionally be substituted by one or more groups selected from $C_1$-$C_{25}$ alkyl which may be optionally interrupted by —O—, or $C_1$-$C_{25}$ alkoxy, $R^1$, $R^2$, $R^3$, $R^4$, $R^5$, and $R^6$ are independently of each other hydrogen, halogen, or an organic substituent, or $R^1$ and $R^2$, $R^4$ and $R^6$, $R^2$ and $R^3$, $R^5$ and $R^3$, and/or $R^5$ and $R^6$, which are adjacent to each other, together form an aromatic or heteroaromatic ring or a ring system which can optionally be substituted, $R^7$ is an organic substituent, wherein two or more substituents $R^7$ in the same molecule may have different meanings, or can form together an aromatic or heteroaromatic ring or ring system, and x is 0, or an integer of 1 to 5;

$A^1$, $A^2$, $A^{1'}$ and $A^{2'}$ are independently of each other a $C_6$-$C_{24}$ aryl group, a $C_2$-$C_{30}$ heteroaryl group, which can optionally be substituted, or a group

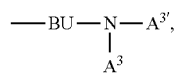

wherein BU is a bridging unit, $A^3$ and $A^{3'}$ are independently or each other a $C_6$-$C_{24}$ aryl group or a $C_2$-$C_{30}$ heteroaryl group, which can optionally be substituted, or $A^1$ and $A^{1'}$ or $A^2$ and $A^{2'}$ or $A^3$ and $A^{3'}$ together with the nitrogen atom to which they are bonded form a heteroaromatic ring or ring system, and $A^3$ and $A^{3'}$ are independently of each other a $C_6$-$C_{24}$ aryl group or a $C_2$-$C_{30}$ heteroaryl group, which can optionally be substituted, or $A^1$ and $A^{1'}$ or $A^2$ and $A^{2'}$ or $A^3$ and $A^{3'}$ together with the nitrogen atom to which they are bonded form a heteroaromatic ring system

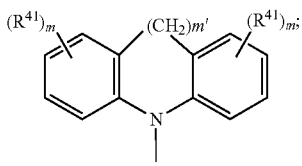

m' is 0, 1, or 2;

$R^{41}$ can be the same or different at each occurrence and is Cl, F, CN, $NR^{45}R^{45'}$, a $C_1$-$C_{25}$ alkyl group, a $C_4$-$C_{18}$ cycloalkyl group, a $C_1$-$C_{25}$ alkoxy group, in which one or more carbon atoms which are not in neighbourhood to each other could be replaced by $-NR^{45}-$, $-O-$, $-S-$, 13 $C(=O)-O-$, or $-O-C(=O)-O-$, and/or wherein one or more hydrogen atoms can be replaced by F, a $C_6$-$C_{21}$ aryl group, or a $C_6$-$C_{24}$ aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ and $R^{45'}$ are independently of each other H, a $C_1$-$C_{25}$ alkyl group, a $C_4$-$C_{18}$ cycloalkyl group, in which one or more carbon atoms which are not in neighbourhood to each other could be replaced by $-NR^{45}-$, $-O-$, $-S-$, $-C(=O)-O-$, or, $-O-C(=O)-O-$, and/or wherein one or more hydrogen atoms can be replaced by F, a $C_6$-$C_{24}$ aryl group, or a $C_6$-$C_{24}$ aryloxy group, wherein one or more carbon atoms can be replaced by O, S, or N, and/or which can be substituted by one or more non-aromatic groups $R^{41}$, and $R^{45''}$ is H, a $C_1$-$C_{25}$ alkyl group or a $C_4$-$C_{18}$ cycloalkyl group, m can be the same or different at each occurrence and is 0, 1, 2, or 3.

$A^4$, $A^{4'}$, $A^6$, $A^7$, $A^8$, $A^5$, $A^{5'}$, $A^{6'}$, $A^{7'}$, and $A^{8'}$ are independently of each other a $C_6$-$C_{24}$ aryl group or a $C_2$-$C_{30}$ heteroaryl group, which can optionally be substituted; with the proviso that phenazine compounds expressed by formula

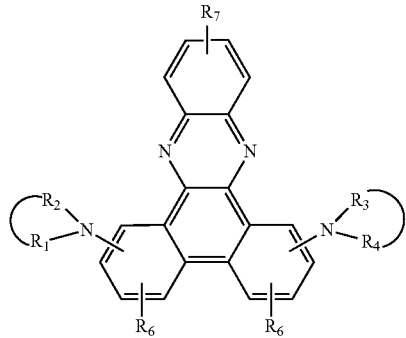

are excluded, wherein:
each $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each $R_5$-$R_7$ is an H atom, (substituted)alkyl group, alkoxy group, halogen atom or nitro group.

9. Solar cells, dye lasers or electroluminescent devices comprising a compound of formula I according to claim 8.

10. A process for the preparation of compounds of the formula Ia or Ib according to claim 8, wherein $Z^1$ and $Z^2$ are independently of each other —$NA^1A^{1'}$, or

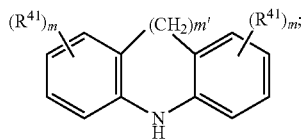

m' is 0, 1, or 2; which comprises reacting a compound of formula

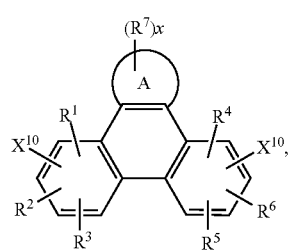   (XX)

wherein $X^{10}$ stands for halogen, with a compound of formula $HNA^1A^{1'}$, or

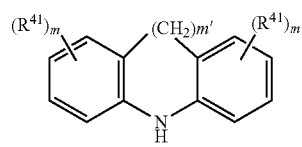

in the presence of a base and a catalyst in a solvent.

11. A compound according to claim 8, of the formula

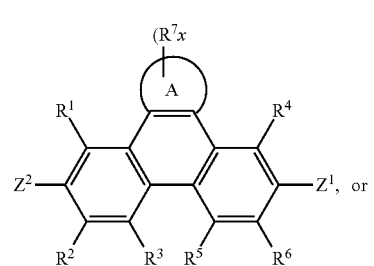   (Ia)

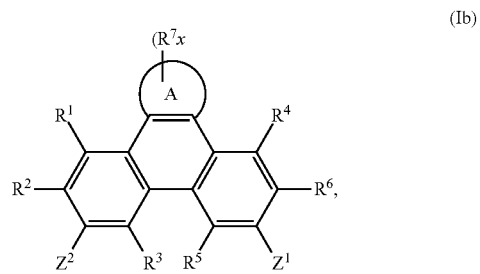   (Ib)

wherein A is a 6-membered heteroaromatic ring, containing one nitrogen atom and at least one further heteroatom selected from nitrogen, substituted nitrogen, oxygen and sulfur, Ar and Ar' are independently of each other phenyl or naphthyl, which may optionally be substituted by one or more groups selected from $C_1$-$C_{25}$alkyl which may optionally be interrupted by —O— or $C_1$-$C_{25}$alkoxy, $A^1$, $A^2$, $A^{1'}$ and $A^{2'}$ are independently of each other a $C_6$-$C_{24}$aryl group, a $C_2$-$C_{30}$heteroaryl group, which can optionally be substituted, or a group

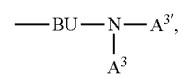

wherein BU is

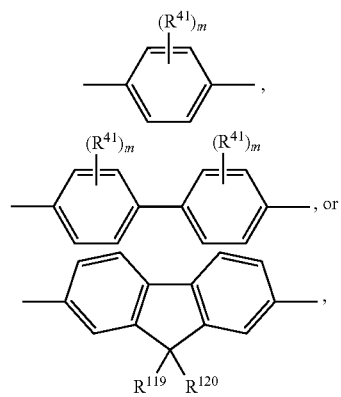

$A^3$ and $A^{3'}$ are independently of each other a $C_6$-$C_{24}$aryl group or a $C_2$-$C_{30}$heteroaryl group, which can optionally be substituted, or A' and A$^{1'}$ or A$^2$ and A$^{2'}$ or A$^3$ and A$^{3'}$ together with the nitrogen atom to which they are bonded form a heteroaromatic ring system

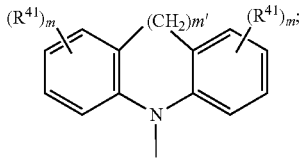

m' is 0, 1, or 2;

R$^{41}$ can be the same or different at each occurrence and is Cl, F, CN, NR$^{45}$R$^{45'}$, a C$_1$-C$_{25}$alkyl group, a C$_4$-C$_{18}$cycloalkyl group, a C$_1$-C$_{25}$alkoxy group, in which one or more carbon atoms which are not in neighbourhood to each other could be replaced by —NR$^{45}$—, —O—, —S—, —C(=O)—O—, or —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or two or more groups R$^{41}$ form a ring system;

R$^{45}$ and R$^{45'}$ are independently of each other H, a C$_1$-C$_{25}$alkyl group, a C$_4$-C$_{18}$cycloalkyl group, in which one or more carbon atoms which are not in neighbourhood to each other could be replaced by —NR$^{45''}$—, —O—, —S—, —C(=O)—O—, or, —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, and R$^{45''}$ is H, a C$_1$-C$_{25}$alkyl group or a C$_4$-C$_{18}$cycloalkyl group, m can be the same or different at each occurrence and is 0, 1, 2, or 3.

* * * * *